United States Patent
Ono et al.

(10) Patent No.: US 8,118,786 B2
(45) Date of Patent: Feb. 21, 2012

(54) GUARDED MEDICAL WINGED NEEDLE ASSEMBLY

(75) Inventors: Seiichi Ono, Oita (JP); Kaoru Maneyama, Tokyo (JP)

(73) Assignee: Kawasumi Laboratories, Inc., Tokyo (JP)

( * ) Notice: Subject to any disclaimer, the term of this patent is extended or adjusted under 35 U.S.C. 154(b) by 893 days.

(21) Appl. No.: 11/391,320

(22) Filed: Mar. 29, 2006

(65) Prior Publication Data

US 2007/0239118 A1 Oct. 11, 2007

(51) Int. Cl.
*A61M 5/32* (2006.01)

(52) U.S. Cl. .......................... 604/198; 604/110

(58) Field of Classification Search ............ 604/110, 604/171, 177, 198, 263, 111, 197
See application file for complete search history.

(56) References Cited

U.S. PATENT DOCUMENTS

| | | | |
|---|---|---|---|
| 5,219,339 A * | 6/1993 | Saito | 604/198 |
| 5,382,240 A * | 1/1995 | Lam | 604/177 |
| 6,200,294 B1 * | 3/2001 | Liu | 604/198 |
| 6,736,798 B2 | 5/2004 | Ohkubo et al. | |
| 7,060,055 B2 * | 6/2006 | Wilkinson et al. | 604/263 |
| 2003/0078540 A1 * | 4/2003 | Saulenas et al. | 604/110 |
| 2006/0047252 A1 | 3/2006 | Ono | |

* cited by examiner

*Primary Examiner* — Kevin C Sirmons
*Assistant Examiner* — Kami A Bosworth
(74) *Attorney, Agent, or Firm* — Oblon, Spivak, McClelland, Maier & Neustadt, L.L.P.

(57) ABSTRACT

A guarded medical winged needle assembly for safely and securely encasing a winged needle without any complicated operation, includes a cylindrical needle cover 1 having a forward section 2, a middle section 3 and a backward section 4, the middle section 3 having an opening 5 formed at a bottom thereof, the backward section 4 having a slit 7, and a winged needle 21 having a pair of wings 24 fitted to on both sides of a hub 23, a needle 22 provided before said hub 23 and a tube T fitted to a backward portion of said hub 23, and said winged needle 21 being slidably housed and protected in said needle cover 1, (A) an engaging member 27, 28 being fitted to said tube T, or (B) an engaging member 30 being fitted to a backward portion of said hub 23, said winged needle thereby being fixable when housed in said needle cover.

4 Claims, 16 Drawing Sheets

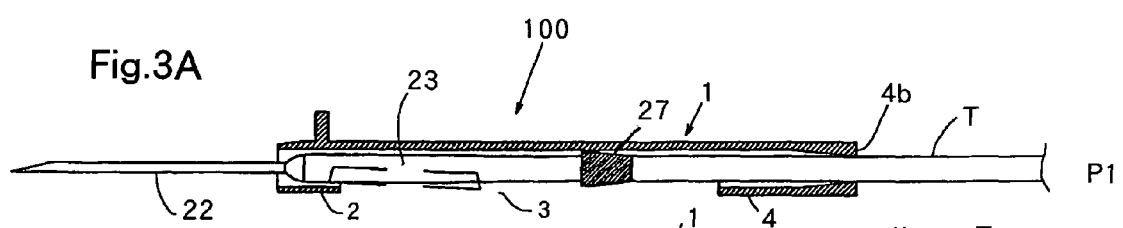
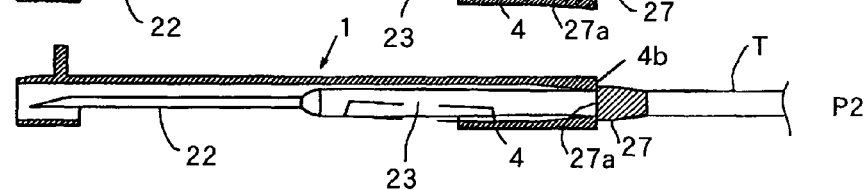
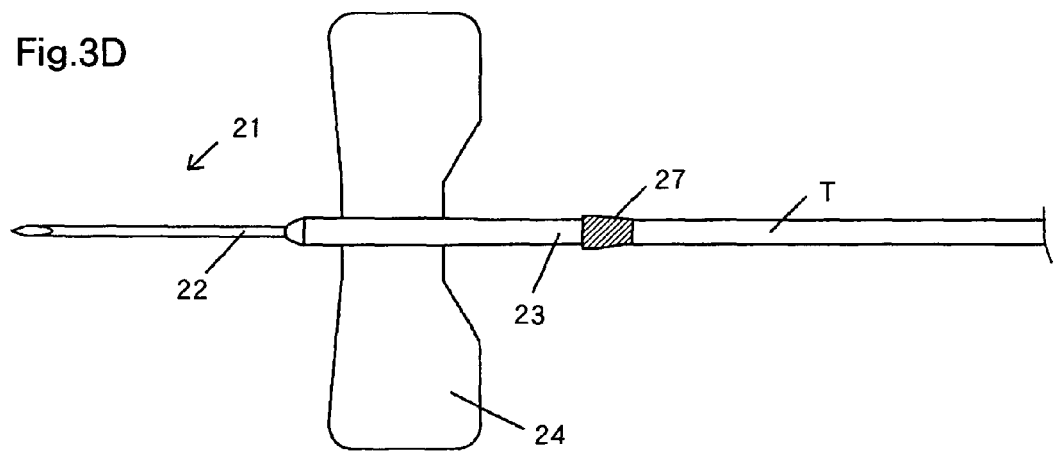

Fig.5A1
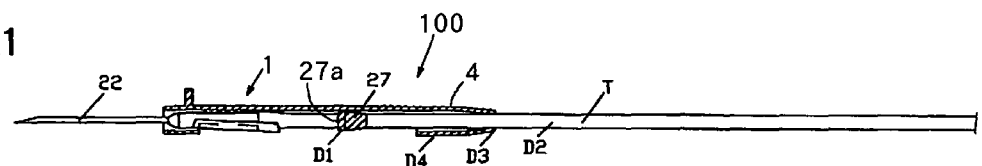
Fig.5A2
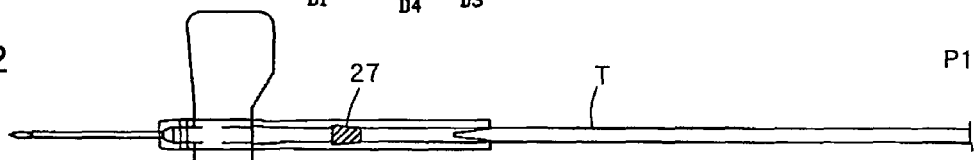
Fig.5B1
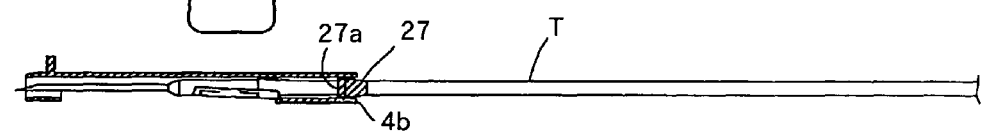
Fig.5B2
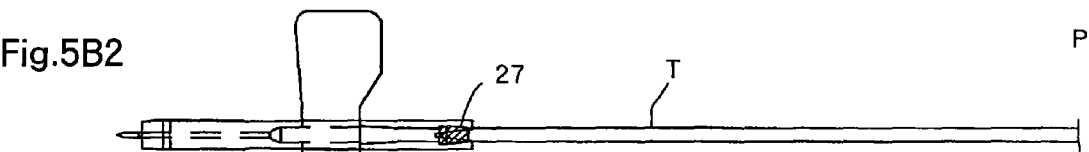
Fig.5C1
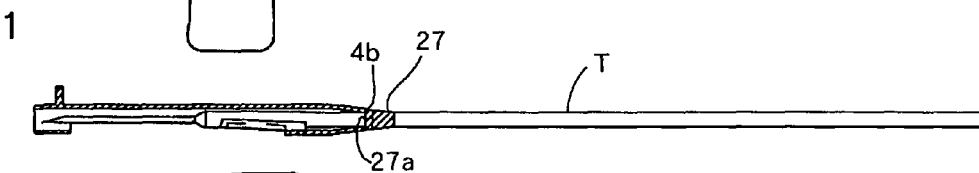
Fig.5C2
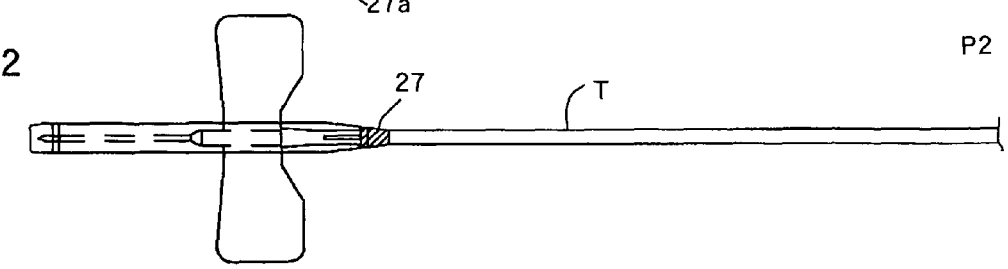

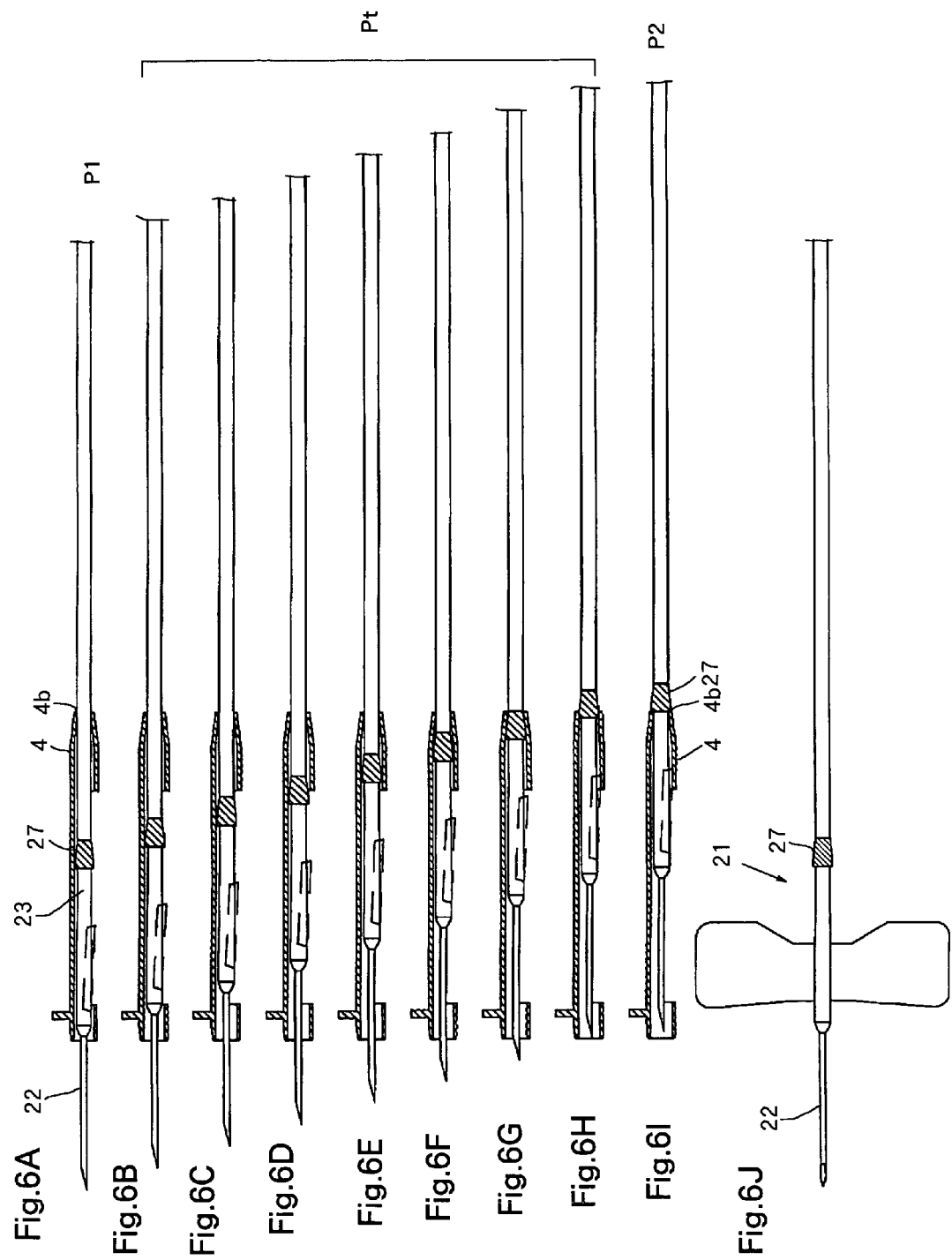

Fig.8A1
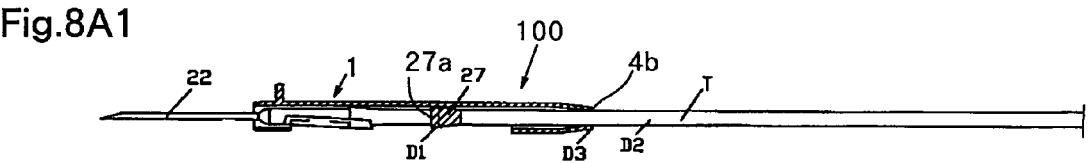
Fig.8A2
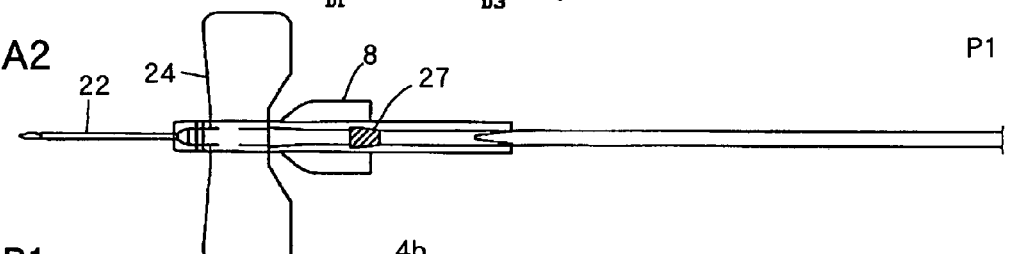
Fig.8B1
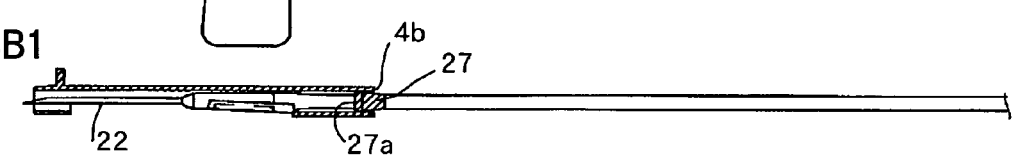
Fig.8B2
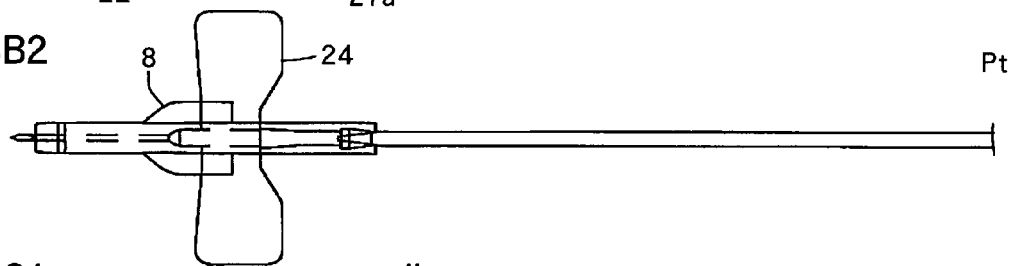
Fig.8C1
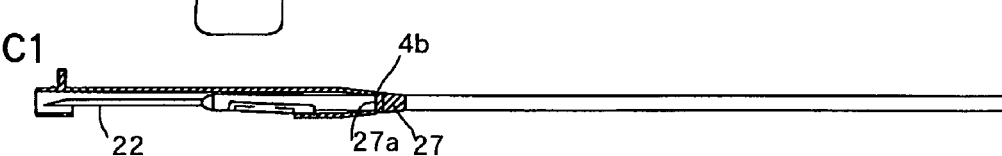
Fig.8C2
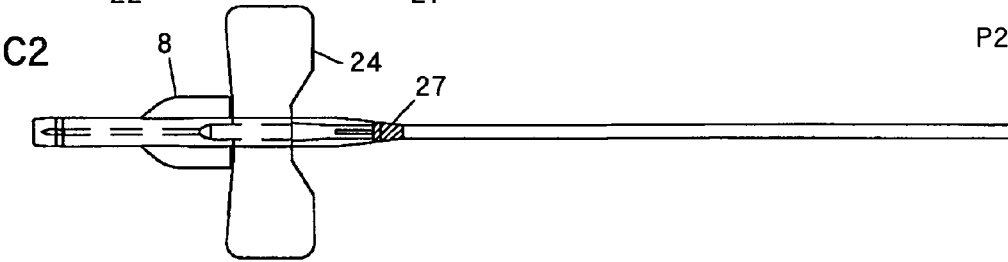

Fig.10A1
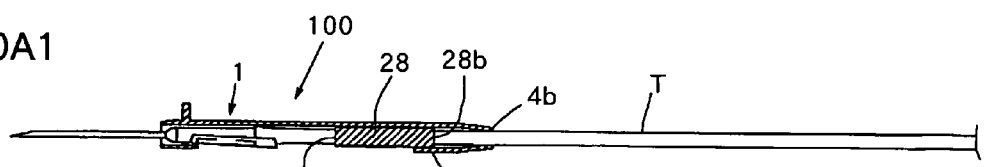
Fig.10A2
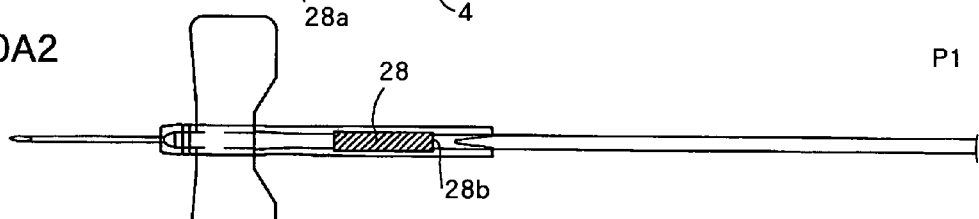
Fig.10B1
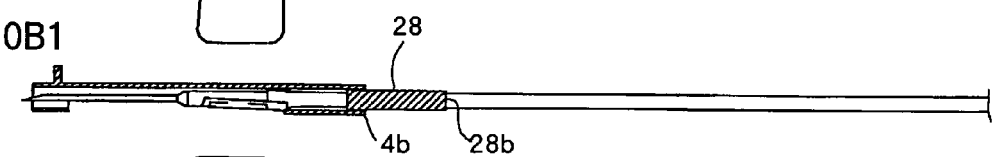
Fig.10B2
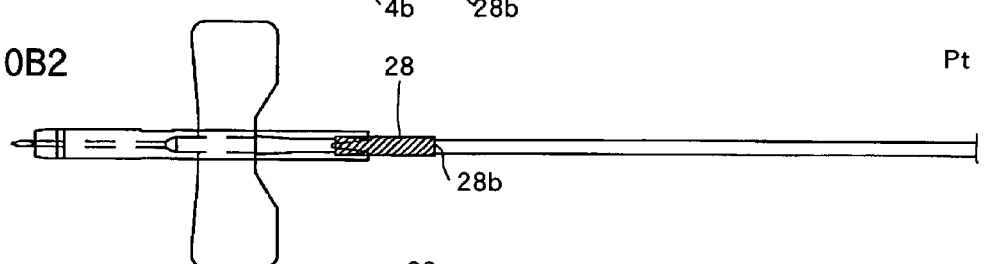
Fig.10C1
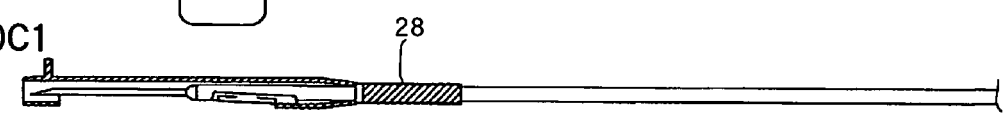
Fig.10C2
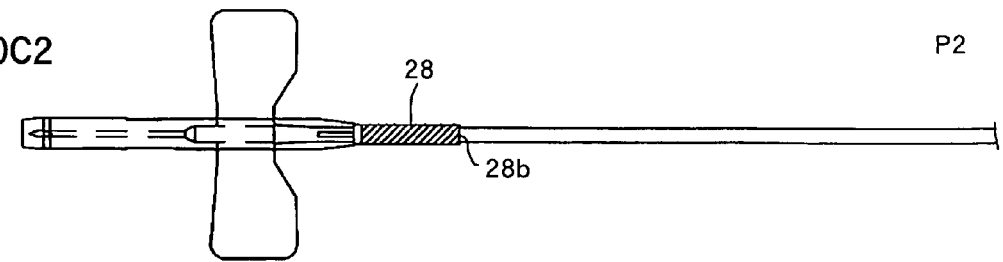

Fig.12A1
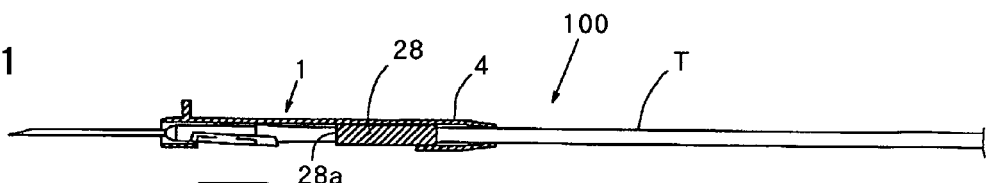
Fig.12A2
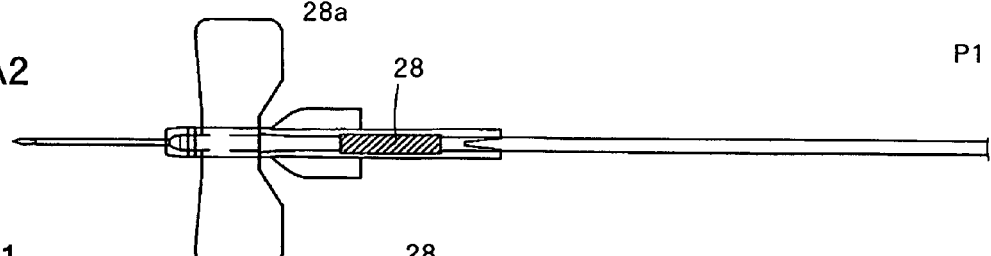
Fig.12B1
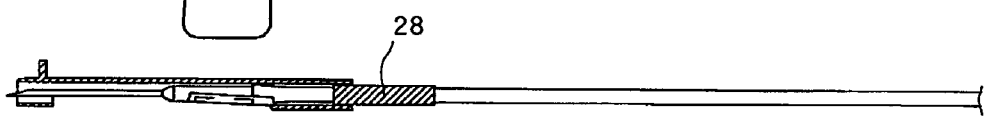
Fig.12B2
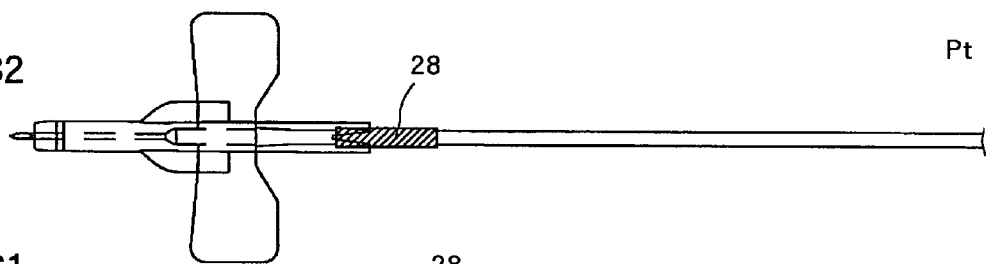
Fig.12C1
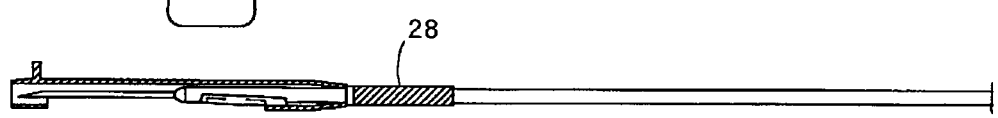
Fig.12C2
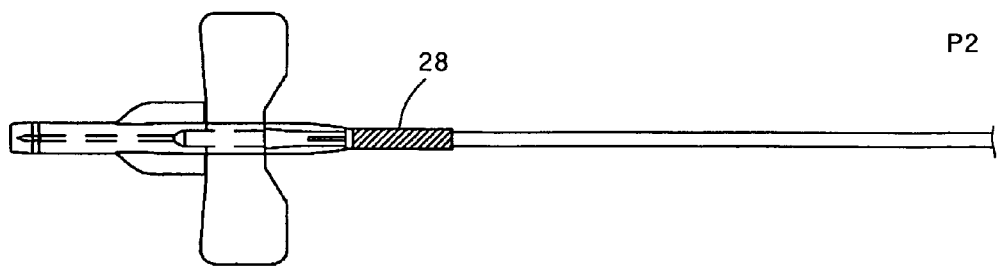

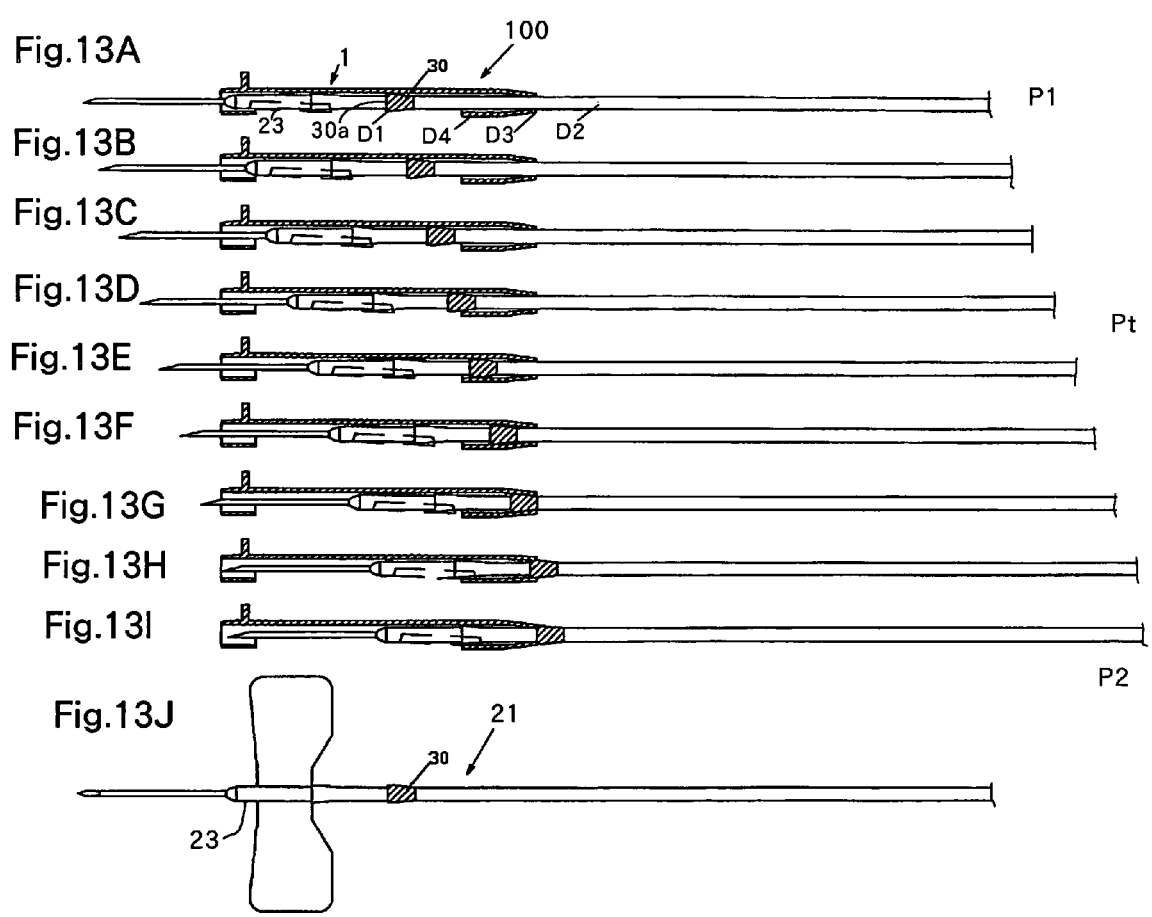

GUARDED MEDICAL WINGED NEEDLE ASSEMBLY

BACKGROUND OF THE INVENTION

1. Field of the Invention

The present invention relates to a medical winged needle assembly such as a PSV (Pediatric Scalp Vein) set, an AVF (Arteriovenous Fistula) set, etc., for dialysis, infusion, blood transfusion and the like. More specifically, it relates to improvements in a guarded medical winged needle assembly and relates to a guarded medical winged needle assembly that is improved in handling while maintaining the reliability and safety thereof.

2. Description of the Related Art

In recent years, with the spread of infectious diseases such as virus hepatitis, AIDS, etc., which are transmitted through a medical needle contaminated with blood or body fluid of a disease carrier, medical institutes have a problem of infections caused by accidental needlesticks of medical staff workers who work on blood transfusion, dialysis, etc. Further, there has been a possibility of a waste disposer being accidentally stuck with a needle to which contaminated blood adheres while he or she is at work.

To address this problem, there have been proposed some guarded medical winged needle assemblies that are capable of safely encasing a used needle. The present inventors have proposed an invention directed to a guarded winged needle assembly with a pair of wing-shaped stoppers disposed on both sides of its middle portion in JP-A-2001-327599 (P2001-327599A). In this invention, a used winged needle is encased in the above needle guard, and then both wings of the winged needle are folded upward, thereby the two wings intersect with, and are engaged with, the wing-shaped stoppers and the winged needle does not protrude from the needle cover.

In JP-A-2003-116996 (P2003-116996A), the present inventors have also proposed that a tube connected to the hub of the above guarded winged needle assembly be fixed into a groove formed in the backward portion of the needle cover for fixing the needle more securely. (U.S. Pat. No. 6,736,798 to the present assignee discloses an invention to the same effect.)

In the above-proposed winged needle assembly, however, the intersection and engagement of the two wings with the wing-shaped stoppers is complicated and needs a considerable skill. In particular, it has not been easy at all for a worker having large inexpert hands to perform the operations of folding the two wings of the winged needle assembly upward and further causing the above two wings to intersect and be engaged with the wing-shaped stopper of the needle cover.

Further, U.S. Pat. No. 5,931,815 to Liu discloses a multi-functional safety infusion set with injection needle retractable in a wing-equipped sheath. Specifically, as shown in FIGS. 3 to 5 attached to the above U.S. patent, the safety infusion set has an upper engaging section 11 with a spiral groove and a lower engaging section 12 with a latch groove formed around the outer periphery of a tube body 10 positioned next to the bottom end of a needle seat 31. When a needle 32 is enclosed in the wing-equipped sheath 4, the lower engaging section 12 slides over a backward end portion (connecting section 411) of the wing-equipped sheath 4 to an outside of the sheath, and the upper engaging section 11 is engaged or screw-fixed with the backward end portion 411 of the wing-equipped sheath 4.

In the invention of the above '815 U.S. patent to Liu, when the needle 32 is to be enclosed in the wing-equipped sheath 4, it is required to perform a double-step operation of causing the lower engaging section 12 to go over the backward end of the wing-equipped sheath 4 first and then causing the upper engaging section 11 to be screw-engaged with the backward portion of the wing-equipped sheath 4. This double-step operation is complicated and troublesome.

Further, U.S. Pat. No. 6,200,294 to Liu discloses syringe with a safety slide sleeve that can receive and hide an injection needle therein. Specifically, the syringe has a tube body 10 positioned next to the backward end of a needle holder 31 and a plurality of axially downward extending and downward tapered guiding ribs 12 formed on the tube body as shown in FIGS. 1 to 5 attached to the above U.S. patent. When an injection needle 3 is received in the safety slide sleeve 4, the guiding ribs 12 slide over an inward extending latching flange 411 on the backward end (bottom portion) of the safety slide sleeve 4 and become to be engaged with the backward wall surface of the safety slide sleeve 4.

The syringe according to the invention of the above U.S. patent to Liu does not have any wing at all, and when the needle is kept in the above safety slide sleeve, the syringe does not permit the operation of fluid infusion, or the like. Further, when the injection needle 3 is received in the safety slide sleeve 4, it is required to cause the plurality of guiding ribs to slide over the backward end of the safety slide sleeve 4, and such an operation hence needs a considerably strong force. The syringe of the above U.S. patent involves a difficulty in operation.

U.S. Pat. No. 5,219,339 to Saito (note: JP-A-H3-158171 as Japanese laid-open publication of family patent) discloses a disposable injection needle integrated with a cap, comprising a cannula N, a body 1 for holding the cannula, the body having a broad columnar body 6, slants 4 and several necks, and a cap 10 having a flange for engagement with the necks, the cap 10 being for engagement with the body 1.

The invention of the above U.S. patent to Saito is not at all directed to any winged needle set. Further, when the cannula N is encased in the needle cap 10, the broad columnar body 6 and the slants 4 are required to go over the backward portion of the needle cap 10, causing such an operation troublesome.

SUMMARY OF THE INVENTION

It is an object of the present invention to provide a guarded medical winged needle assembly having a needle cover in which a winged needle can be safely and securely encased without any complicated operation.

According to the present invention, there are provided;

[1] a guarded medical winged needle assembly comprising a generally cylindrical needle cover (1) having a forward section (2), a middle section (3) and a backward section (4) in this order in the longitudinal direction of a tubular member, the middle section (3) having an opening (5) formed at the bottom thereof, the backward section (4) having a slit (7), and a winged needle (21) having a pair of wings (24) attached to on both sides of a hub (23), a needle (22) attached to the front portion on said hub (23) and a tube (T) fitted to a backward portion of said hub (23), said winged needle (21) being housed slidably and protected in said needle cover (1), wherein (A) an engaging member (27), (28) being fitted to said tube (T), or (B) an engaging member (30) being fitted to the backward portion of said hub (23), said engaging member (27), (28), (30) thereby keeps said winged needle fixed, when housed in said needle cover (1),

[2] a guarded medical winged needle assembly as recited in above [1], wherein said engaging member (27), (28), (30) passes said backward section (4) having said slit (7) while outwardly expanding the backward section (4) along the slit (7) when said needle (22) slidably moves in the needle cover (1) from a first position (Position 1) wherein said needle (22) is exposed from the forward section of said needle cover (1) to a second position (Position 2) wherein said needle (22) is retracted and hided in said needle cover (1), and after said needle (22) is moved to said second position, a front surface of said engaging member (27), (28), (30) is engaged with a backside surface (4b) of said backward section (4), thereby said winged needle is being fixed in said second position in said needle cover and being kept from moving again toward the first position,

[3] a guarded medical winged needle assembly as recited in above [1] or [2], wherein, when said needle (22) is in said first position where said needle (22) is exposed from the forward section of said cover (1), front surface of said wings (24) of said winged needle (21) are in contact with a backside surface of said forward section (2) in a state where said needle (22) is exposed from the forward section (2) of said needle cover and said engaging member (27), (28), (30) is positioned in said middle section (3) or said backward section (4), and when said winged needle (21) is in said second position where said winged needle (21) is retracted and hided in the needle cover (1), said needle (22) is positioned in said forward section (2) or said middle portion (3), said engaging member (27), (28), (30) is exposed from said backward section (4) and a front surface thereof is engaged with a backside surface of said backward section (4), thereby said winged needle is being fixed in said second position in said needle cover (1),

[4] a guarded medical winged needle assembly as recited in any one of above [1] to [3], wherein said engaging member (27), (28), (30) has an outer diameter (D1), said tube (T) has an outer diameter (D2), the opening (4a) of said backward section (4) has a diameter (D3) and said backward section (4) has an inner diameter (D4), and the outer diameter (D1), the outer diameter (D2), the diameter (D3) and the inner diameter (D4) satisfy the following relationships (i) to (iii), Outer diameter (D1) of engaging member (27), (28), (30)>Outer diameter (D2) of tube (T)    (i)

Outer diameter (D1) of engaging member (27), (28), (30)>Diameter (D3) of opening 4a of backward section (4)    (ii)

Outer diameter (D1) of engaging member (27), (28), (30)≦Inner diameter (D4) of backward section 4    (iii),

[5] a guarded medical winged needle assembly as recited in any one of above [1] to [4], wherein a pair of stoppers (8) for being engaged with the wings (24) are protruded on both sides of said middle section (3),

[6] a guarded medical winged needle assembly comprising a cylindrical needle cover (1') having a forward section (2), a middle section (3) and a backward section (4) in this order in the longitudinal direction of a tubular member, the long middle section (3) having an opening (5) formed at a bottom thereof, and a winged needle (21) having a pair of wings (24) fitted to on both sides of a hub (23), a needle (22) attached to the front portion of said hub (23) and a tube (T) fitted to a backward portion of said hub (23), said winged needle (21) being housed slidably and protected in said needle cover (1'), wherein an engaging member (40), (50), (60) having a hook (41), (51), (61) is being fitted to said tube (T) or to the backward portion of said hub (23), said engaging member (40), (50), (60) thereby keeps said winged needle fixed, when housed in said needle cover (1'),

[7] a guarded medical winged needle assembly as recited in the above [6], wherein the hook (41), (51), (61) of said engaging member (40), (50), (60) pass an inside of said backward section (4) while being inwardly sagged when said needle (22) slidably moves in the needle cover (1) from a first position (Position 1) where said needle (22) is exposed from the forward section of said needle cover (1') to a second position (Position 2) where said needle (22) is retracted and hided in said needle cover (1'), and after said needle (22) is moved to the second position, front surface of said hook (41), (51), (61) is engaged with a backside surface (4b) of said backward section (4), thereby said winged needle is being fixed in said second position in said needle cover and being kept from moving again toward the first position,

[8] a guarded medical winged needle assembly as recited in the above [6] or [7], wherein, when said needle (22) is in said first position where said needle (22) is exposed from the forward section of said cover (1'), front surfaces of said wings (24) of said winged needle (21) are in contact with a backside surface of said forward section (2) in a state where said needle (22) is exposed from the forward section (2) of said needle cover (1') and said engaging member (40), (50), (60) is positioned in said middle section (3) or said backward section (4), and when said winged needle (21) is in said second position wherein said winged needle (21) is retracted and hided in the needle cover (1'), said needle (22) is placed in said forward section (2) or said middle section (3), the hook (41), (51), (61) of said engaging member (40), (50), (60) is exposed from said backward section (4) and a front surface thereof are engaged with a backside surface (4b) of said backward section (4), thereby said winged needle is being fixed in said second position in said needle cover, and

[9] a guarded medical winged needle assembly as recited in any one of the above [6] to [8], wherein the hook (41), (51), (61) of said engaging member (40), (50), (60) has an outer diameter (D1), said tube (T) has an outer diameter (D2), the opening (4a) of said backward section (4) has a diameter (D3) and said backward section (4) has an inner diameter (D4), and the outer diameter (D1), the outer diameter (D2), the diameter (D3) and the inner diameter (D4) satisfy the following relationships (i) to (iii), Outer diameter (D11) of hook (41), (51), (61) >Outer diameter (D2) of tube (T)    (i)

Outer diameter (D11) of hook (41), (51), (61) >Diameter (D3) of opening (4a) of backward section (4)    (ii)

Outer diameter (D11) of hook (41), (51), (61) >Inner diameter (D4) of backward section (4)    (iii).

(Advantageous Effect of the Invention)

The guarded medical winged needle assembly of the present invention has the following advantageous effect. That is, when the needle 22 is moved from the first position where the needle 22 is exposed from the needle cover 1 to the second position where the needle 22 is encased in the needle cover 1, the engaging member 27, 28, 30 passes through the backward section 4 of the needle cover 1 while outwardly expanding the backward section 4 along the slit 7, and after the needle 22 moves to the second position, the front surface of the engaging member 27, 28, 30 is engaged with the backside surface of the backward section 4 and hence keeps the needle 22 from moving back toward the first position. It is possible that the winged needle 21 is retracted only by pulling the tube T, thereby the engaging member 27, 28, 30 easily slides over the backward section of the needle cover 1 to be engaged, so that the guarded medical winged needle assembly of the present invention is excellent in handling.

Further, the guarded medical winged needle assembly of the present invention also has the following advantageous effect. That is, when the needle 22 is moved from the first position where the needle 22 is exposed before the needle cover 1 to the second position where the j needle 22 is encased in the needle cover 1, the hook 41, 51, 61 of the above engaging member 40, 50, 60 passes an inside of the backward section 4 while inwardly sagging, and after the needle 22 moves to the second position, the front surfaces of the hook 41, 51, 61 are engaged with the backside surface of the backward section 4 and hence keeps the needle 22 from moving back toward the first position. It is possible that the winged needle 21 is retracted only by pulling the tube T, and the engaging member 40, 50, 60 easily passes through the backward section of the needle cover 1 to be engaged, so that the guarded medical winged needle assembly of the present invention is excellent in handling.

BRIEF DESCRIPTION OF THE DRAWINGS

FIG. 1 is a schematic drawing of one embodiment of the needle cover in the present invention, in which

FIG. 2 is a schematic drawing of one embodiment of the needle cover in the present invention, in which

FIG. 3 shows one embodiment of method of use of a guarded medical winged needle assembly, in which FIGS. 3A to 3C are cross-sectional views showing a use process through time, and FIG. 3D is a plan view of a winged needle.

FIG. 4 shows one embodiment of method of use of a guarded medical winged needle assembly, in which

FIG. 5 shows one embodiment of method of use of a guarded medical winged needle assembly, in which FIGS. 5A1, 5B1 and 5C1 are cross-sectional views showing a use process through time, and FIGS. 5A2, 5B2 and 5C2 are plan views showing a use process through time.

FIG. 6 shows one embodiment of method of use of a guarded medical winged needle assembly, in which FIGS. 6A to 6I are cross-sectional views showing a use process through time, and FIG. 6J is a plan view of a winged needle.

FIG. 7 shows one embodiment of method of use of a guarded medical winged needle assembly, in which

FIG. 8 shows one embodiment of method of use of a guarded medical winged needle assembly, in which FIGS. 8A1, 8B1 and 8C1 are cross-sectional views showing a use process through time, and FIGS. 8A2, 8B2 and 8C2 are plan views showing a use process through time.

FIG. 9 shows one embodiment of method of use of a guarded medical winged needle assembly, in which

FIG. 10 shows one embodiment of method of use of a guarded medical winged needle assembly, in which FIGS. 10A1, 10B1 and 10C1 are cross-sectional views showing a use process through time, and FIGS. 10A2, 10B2 and 10C2 are plan views showing a use process through time.

FIG. 11 shows one embodiment of method of use of a guarded medical winged needle assembly, in which

FIG. 12 shows one embodiment of method of use of a guarded medical winged needle assembly, in which FIGS. 12A1, 12B1 and 12C1 are cross-sectional views showing a use process through time, and FIGS. 12A2, 12B2 and 12C2 are plan views showing a use process through time.

FIG. 13 shows one embodiment of method of use of a guarded medical winged needle assembly, in which FIGS. 13A to 13I are cross-sectional views showing a use process through time, and FIG. 13J is a plan view of a winged needle.

FIG. 14 shows another embodiment of method of use of a guarded medical winged needle assembly, in which

FIG. 15 shows another embodiment of method of use of a guarded medical winged needle assembly, in which

FIG. 16 shows another embodiment of method of use of a guarded medical winged needle assembly, in which

Figure 1A:
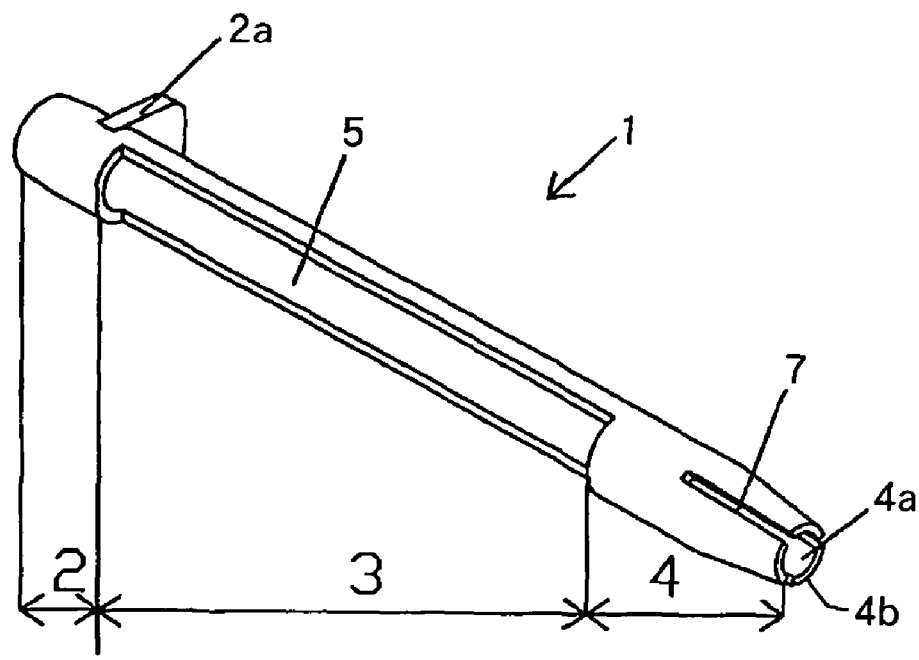
FIG. 1A is a front perspective view of a needle cover with taper.

Reference numerals used in the drawings to the present invention indicate as follows. 1,1': needle cover, 2: forward section, 2a: projection, 3: middle section, 4: backward section, 4a: opening of backward section, 4b: end surface thereof, 5: opening, 7: slit, 8: (wing-shaped) stopper, 21: winged needle, 22: needle, 23: hub, 24: wing, 27: (ring-shaped) engaging member, 27a: front surface thereof, 28: (pipe-shaped) engaging member, 28a: front surface thereof, 28b: backward portion (end surface) thereof, 30: engaging member fitted to, or formed on, hub, 30a: front surface thereof, 40: engaging member, 41: hook, 42: engaging member body, 43: connecting portion, 50: engaging member, 51: hook, 52: engaging member body, 60: engaging member, 61: hook, 62: engaging member body, 63: connecting portion, 65: annular fixing member, 100: guarded medical winged needle assembly, D1: outer diameter of engaging member, D2: outer diameter of tube, D3: diameter of opening 4a of backward section 4, D4: inner diameter of backward section 4, T: tube.

DESCRIPTION OF THE PREFERRED EMBODIMENTS

Preferred Embodiments of the guarded medical winged needle assembly 100 of the present invention will be explained with reference to drawings hereinafter.

(Guarded Medical Winged Needle Assembly)

As shown in FIGS. 3 to 13, basically, the guarded medical winged needle assembly of the present invention comprises a needle cover (guard) 1 having a forward section 2, an opening 5 formed in a middle section thereof and a slit 7 formed in a backward section 4 thereof, and a winged needle 21 having a pair of wings 24 fitted to a hub 23, a needle 22 attached to a front portion of the hub 23 and a tube T fitted or connected to a backward portion of the hub 23. The winged needle 21 is slidably encased in the needle cover 1.

Figure 1B:
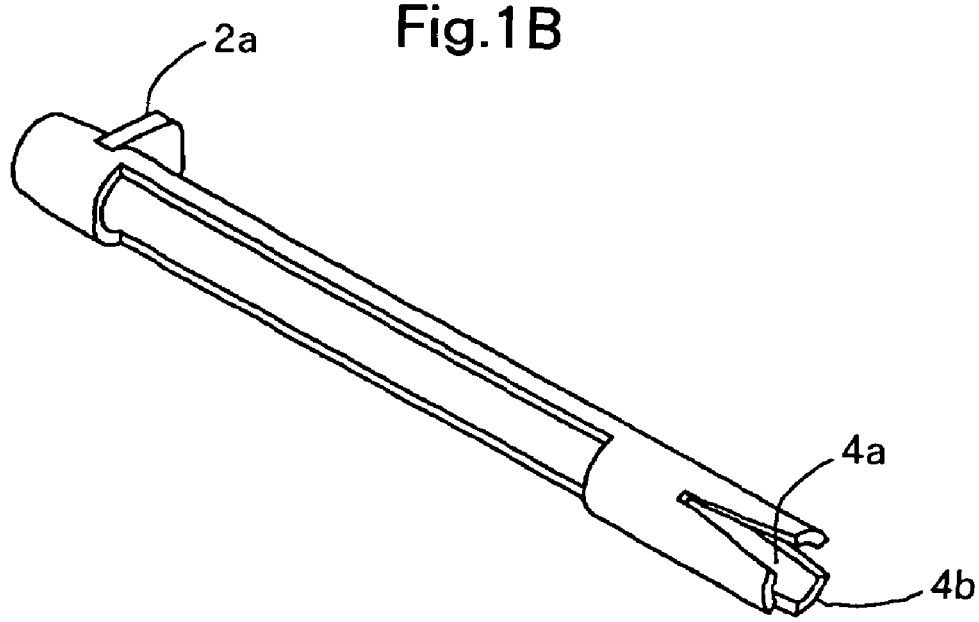
FIG. 1B is a front perspective view showing a state without taper.

The needle cover 1 has a tubular member or body as shown in FIGS. 1A and 1B, and the tubular member forming the needle cover 1 is longitudinally divided into three sections, thus, the forward section 2, the middle section 3 and the backward section 4, and the opening or aperture 5 is formed at the bottom of the middle section 3 in a manner in which nearly half of the periphery in a cross section of the middle section 3 is removed. Further, the slit 7 is being formed in the backward section 4.

The needle cover 1 is preferably formed from a semi-hard material. The semi-hard material preferably includes semi-hard thermoplastic resins such as polyethylene, polypropylene, polybutene, polystyrene, a methacrylic resin, polycarbonate, polyvinyl chloride, an ethylene tetrafluoride resin, polyamide and polyethylene terephthalate.

The semi-hard material is preferred as a material for the needle cover for the following reasons. The semi-hard material desirably has rigidity sufficient enough for functioning as a guard (sheath) to fully protect an encased winged needle from an impact or shock, and it is also desirably so elastic as to deform to some extent to broaden or widen the opening 4a of the backward section, thereby permitting the hub, etc., of the encased winged needle to be withdrawn through the opening 4a.

One slit 7 or a plurality of slits 7 (two or more slits) may be formed in the backward section 4. The number of the slit(s) 7 is not specifically restricted, nor is the form thereof. When the needle 22, attached to the front portion of the hub 23, is retracted into the needle cover 1 after use, the backward portion of the hub 23 accordingly protrudes out of the opening 4a of the backward section 4 of the needle cover 1 together with an engaging member as will be explained later. The form, number, etc., of the slit(s) 7 are, as mentioned above, not specially limited so long as the portion including the slit(s) has good flexibility and is outwardly expandable, thereby enough expansion of the opening 4a is made to facilitate the above withdrawal or protrusion of the backward portion of the hub through the opening 4a during the above retraction.

Figure 2A:
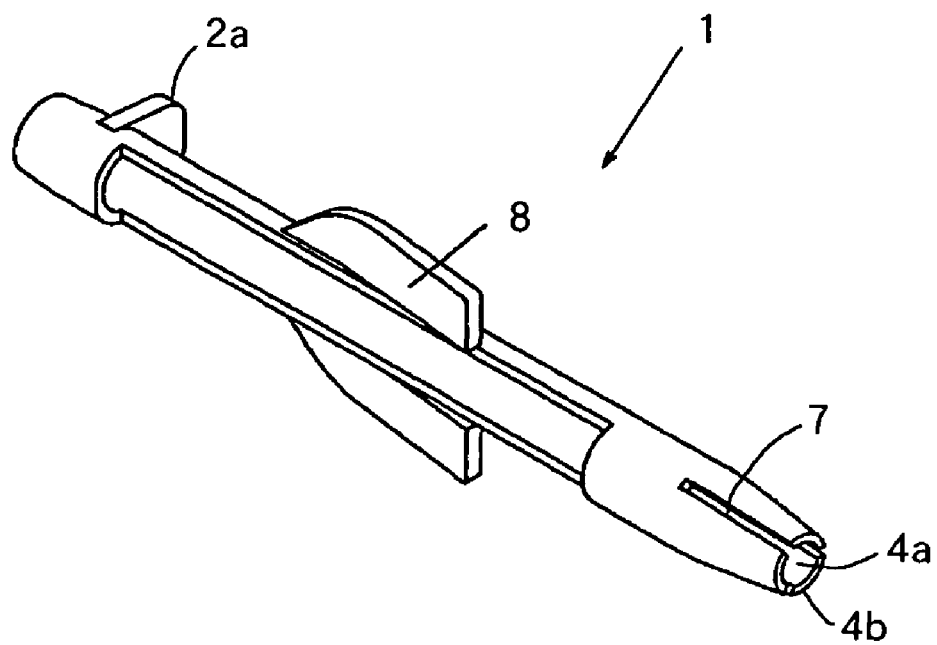
FIG. 2A is a front perspective view of a needle cover with taper.
Figure 2B:
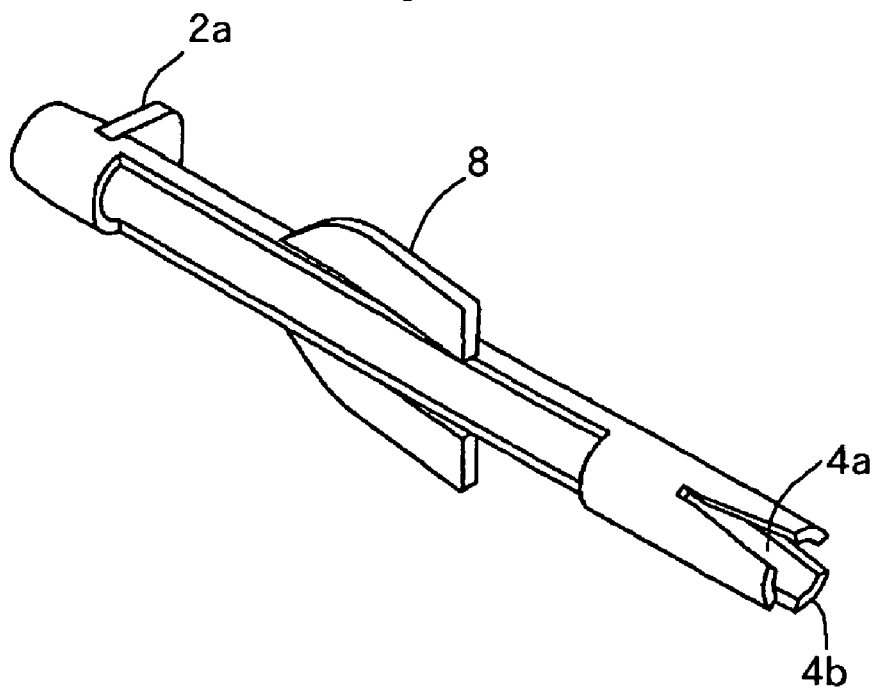
FIG. 2B is a front perspective view showing a state without taper.

Further, the backward section 4 may have a shape in which its external form is tapered toward a backward end portion as shown in FIGS. 1A and 2A. Alternatively, the backward section 4 may have a shape wherein it has a straight external form with no taper and the thickness of its inner wall is increased toward the backward end portion thereof so that its internal hollow portion is tapered, as shown in FIGS. 1B and 2B. In these Figures, reference numeral 4b indicates an end surface (backside surface) of the backward section of the needle cover. The end surface 4b comes in contact with the engaging member under pressure and fixed. The fixed-engaging member keeps the hub at this position thereby preventing the needle 22 from returning and protruding again out of the needle cover 1 as is shown in FIG. 3A.

Further, a pair of wing-shaped stoppers 8 may be formed (fitted) on both sides of the middle section 3 as shown in FIGS. 2A and 2B as required. The stoppers 8 intersect with the wings 24 and work to fix the needle 12 as described in the forgoing JP-A-2001-327599. The stoppers 8 are shaped in the form of a wing each, and made slanted toward the backward section 4 (upwardly to some extent). Employable variations with regard to the form, etc., of the stoppers 8 are described in JP-A-2001-327599 and are incorporated by reference into the present specification.

Further, preferably, a projection 2a is provided in the forward section of the needle cover 1. The projection 2a refers to a portion that a medical worker grasps with his or her fingers when he or she uses the guarded winged medical needle assembly of the present invention.

In the winged needle 21 of the present invention, for example, a pair of the wings 24 are fitted on both sides of the hub 23, the needle 22 is provided on the front portion of the hub 23 and a tube T is fitted (connected) to the backward portion of the hub 23 as shown in the plan view of FIG. 3D. The winged needle 21 is slidably accommodated or housed in the above needle cover 1 to be protected, for example, as shown in FIGS. 3A to 3C.

The operation or use method of the winged needle housed in the needle cover will be explained later with reference to FIGS. 4 to 13.

(Engaging Member 27, 28, 30)

In the present invention, an engaging member 27, 28 is fitted to the above tube T as shown in FIGS. 3 to 12, or an engaging member 30 is fitted to, or formed in, the backward portion of the above hub 23 as shown in FIG. 13. The engaging member can fix the winged needle accommodated or housed in the needle cover.

The engaging member 27 that fits to the tube T may have the form of a ring (having a relatively short and nearly cylindrical form) as shown in FIGS. 3 to 8, or the engaging member 28 may have the form of a pipe (having a relatively long and nearly cylindrical form, or a tube-like form) as shown in FIGS. 9 to 12. The engaging member in a form of ring or a pipe may have a straight form (constant diameter) as shown in FIGS. 9 to 12 or may have a tapered form (decreasing diameter) as shown in FIGS. 3 to 8.

An engaging member 30 that is formed or fitted to the backward portion of the hub 23 may have the form of a ring as shown in FIG. 13, or may have the form of the above-described pipe or a wedge (also referred to as "hook").

The hub 23 and the engaging member 27, 28, 30 are preferably formed by injection molding from a semi-hard thermoplastic resin similar to the material for forming the needle cover. The semi-hard thermoplastic resin includes polyethylene, polypropylene, polybutene, polystyrene, a methacrylic resin, polycarbonate, polyvinyl chloride, an ethylene tetrafluoride resin, polyamide, rubber, elastomer and polyethylene terephthalate. The formed engaging member 27, 28, 30 is fitted to the tube T or the outer surface (circumference) of the hub, in the form of a tube of a ring, with a fixing means such as an adhesive.

When the engaging member 30 is provided to the hub 23, the engaging member 30 can be formed on the backward portion of the hub integrally with the hub 23 when the hub 23 is formed from a semi-hard plastic material by injection molding, or the like. Naturally, the engaging member 30 formed from a semi-hard plastic material separately may be fitted to the hub with a fixing means such as an adhesive as described above.

Further, the engaging member 27, 28, 30 may have a tapered projection (called "hook" also) formed on a circumference thereof.

(Engagement Function of Engaging Member)

In the guarded medical winged needle assembly 100 of the present invention, when the needle 22 slides from a first position (Position 1), wherein it is exposed from the forward section of the needle cover 1 (for example, as shown in FIG. 3A), to a second position (Position 2), where the needle 22 is retracted and hided in the needle cover 1 (for example, as shown in FIG. 3C), the engaging member 27, 28, 30 passes the backward section 4 while it outwardly expands the backward section 4 along the slit 7 of the backward section 4, and after the needle 22 slidably moves to the above second position, the front surface 27a, 28a, 30a of the engaging member 27, 28, 30 is engaged with the backside surface (more specifically, the end surface 4b) of the backward section 4, thereby the winged needle is being fixed in the second position in the needle cover and is kept or prevented from moving again back to the first position.

Further, in the guarded medical winged needle assembly 100 of the present invention, when the above winged needle 21 is in the first position (e.g., FIG. 3A) where the above needle 22 is exposed before (or from the forward section of) the needle cover 1, the front surfaces of the above wings 24 come in contact with a backside surface of the above forward section 2 in a state where the needle 22 is exposed from the forward section 2 of the needle cover 1, and the above engaging member 27, 28, 30 is positioned inside the middle section 3 or the above backward section 4. When the winged needle 21 is in the second position (e.g., FIG. 3C) where the needle 22 is retracted and hided in the needle cover 1, the needle 22 is positioned or placed in the forward section 2 or the above middle section 3, the engaging member 27, 28, 30 is exposed from the backward section 4, and the front surface thereof 27a, 28a, 30a is engaged with the backside surface 4b of the backward section 4, thereby the winged needle is fixed in the second position in the needle cover.

In the guarded medical winged needle assembly 100 of the present invention, preferably, the outer diameter D1 of the engaging member 27, 28, 30, the outer diameter D2 of the tube T, the diameter D3 of the opening 4a of the backward section 4 and the inner diameter D4 of the backward section 4 satisfy the following relationships (i) to (iii), for example, as shown in FIGS. 5, 8 and 13.

Outer diameter D1 of engaging member 27, 28, 30>Outer diameter D2 of tube T  (i)

Outer diameter D1 of engaging member 27, 28, 30>Diameter D3 of opening 4a of backward section 4  (ii)

Outer diameter D1 of engaging member 27, 28, 30≦Inner diameter D4 of backward section 4  (iii)

When the engaging member 27, 28, 30 has a tapered portion, for example, as shown in FIG. 5, the outer diameter D1 thereof is the diameter of a portion having the largest diameter. Further, when the backward section 4 has a tapered portion, for example, as shown in FIG. 5, the inner diameter D4 of the backward section 4 is the diameter of a portion having the largest diameter.

The guarded medical winged needle assembly of the present invention will be explained below with regard to one embodiment of use thereof with reference to drawings.
(Method of Use of Guarded Medical Needle Assembly)(i) (FIGS. 3 to 6)

In FIGS. 3 to 6, FIGS. 3A, 4A, 5A and 6A show the first position (P1) in which the needle 22 is exposed before the needle cover 1 (or exposed from the forward section of the cover 1), and FIGS. 3C, 4C, 5C and 6I show the second position (P2) in which the needle 22 is encased and protected in the needle cover 1. FIGS. 3B, 4B, 5B and FIGS. 6B to 6H show a transition position (Pt) in which the needle 22 is in transition from the first position (P1) to the second position (P2).

(1) In a state where the injection of fluid or the like into a patient is completed, the needle 22 is in the first position wherein the needle 22 is exposed before the needle cover 1. This state is shown in FIGS. 3A, 4A, 5A and 6A.

Figure 4A:
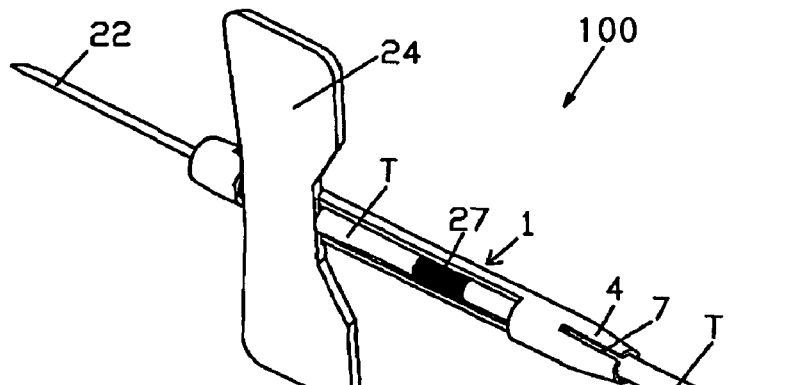
FIGS. 4A to 4C are perspective view of a use process through time.
Figure 4B:
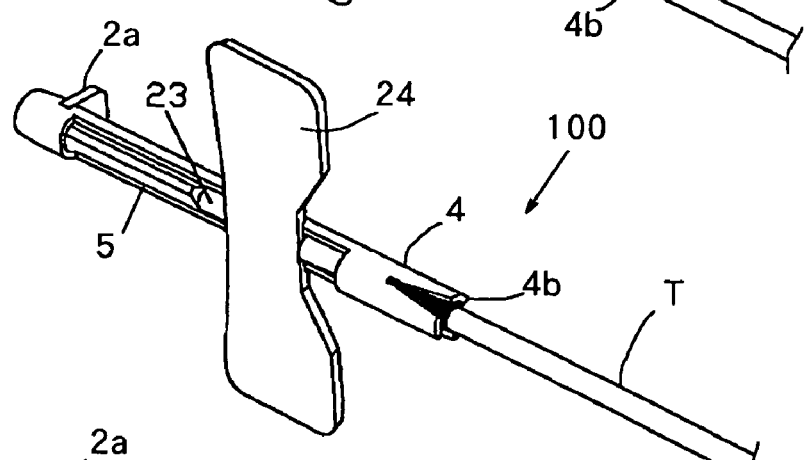
Figure 4C:
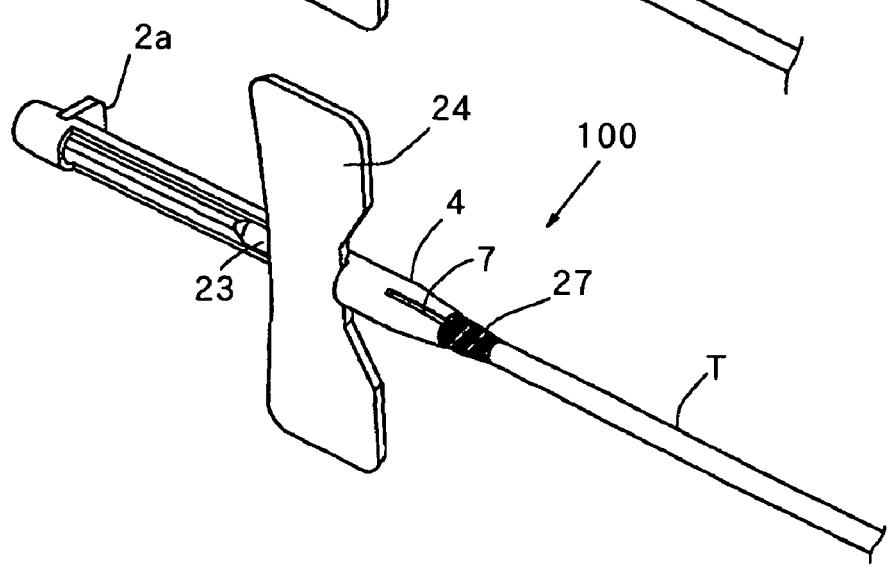

(2) For moving the needle 22 from the first position to the second position, the needle cover 1 is fixed with one hand, and the tube T is withdrawn backward with the other hand to move the tube out of the backward opening 4a of the backward section 4 of the needle cover 1. FIGS. 3B, 4B and 5B show a state where the ring-shaped engaging member 27 is passing through the backward opening 4a.

FIGS. 6B to 6H show the above withdrawing process further in detail. The ring-shaped engaging member 27 moves toward the backward section 4, passes the opening 4a while outwardly expanding the backward section 4 along the slit 7 and passes through the backward section 4. The slit 7 is formed in the backward section 4, thereby the backward section 4 is expanded flexibly outward, and the expanded backward opening 4a particularly serves to make a move of the engaging member 27 out easier.

(3) In a state where the engaging member 27 moves out of the backward opening 4a of the backward section, that is, the needle 22 moves to the second position wherein it is encased in the needle cover 1, a front surface 27a of the engaging member 27 comes in contact with the backside surface 4b of the backward section 4 (more specifically, the end surface 4b of the opening of the backward section) under pressure, so that the engaging member 27 is engaged with the backside surface 4b of the backward section 4. That is, since the outer diameter D1 of the engaging member 27 is greater than the diameter D3 of the backward opening 4a of the backward section 4, the front surface 27a of the engaging member 27 comes in contact with the end surface 4b of the backward section 4 under pressure, thereby the end surface 4b of the backward section 4, together with the fixed engaging member 27, prevents the tube from moving back into the backward section 4. After the needle 22 is retracted and encased in the needle cover 1, therefore, there is no likelihood that the needle 22 moves back toward the first position to expose its acute needlepoint.
(Method of Use of Guarded Medical Winged Needle Assembly) (ii) (FIGS. 7 and 8)

FIGS. 7 and 8 show one embodiment of use method when a wing-shaped stoppers 8 are formed on the needle cover 1. Basically, the guarded medical winged needle assembly in this case is handled in the same manner as in the above explanation.

Figure 7A:
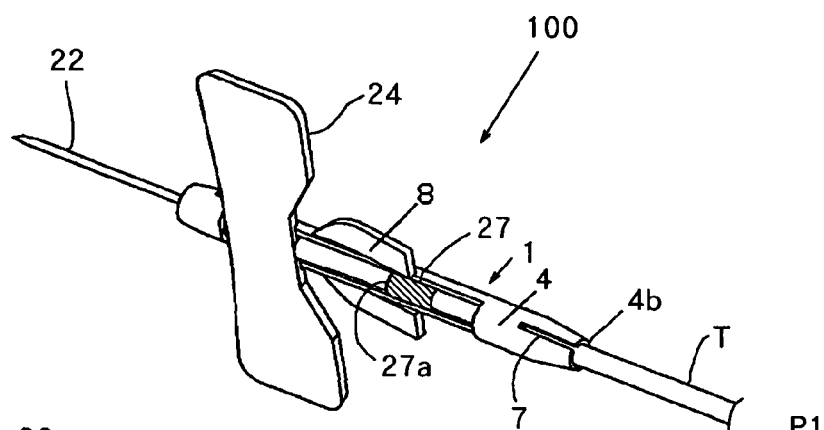
FIGS. 7A to 7C are perspective views showing a use process through time.
Figure 7B:
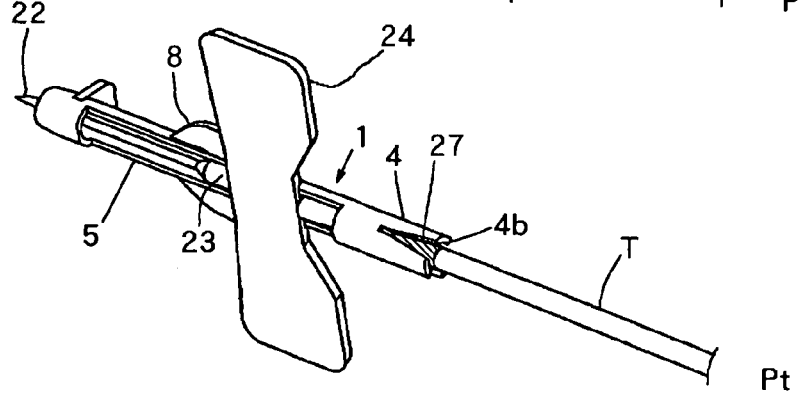
Figure 7C:
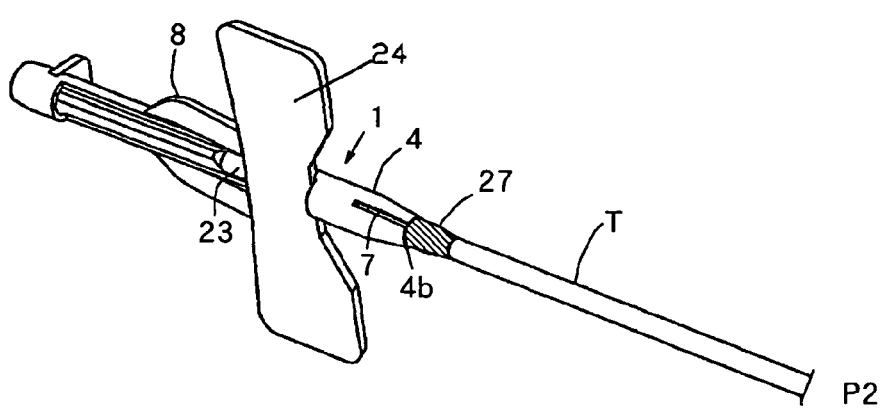

In FIGS. 7 and 8, FIG. 7A and FIG. 8A show the first position (P1) in which the needle 22 is exposed before the needle cover 1, and FIGS. 7C and 8C show the second position (P2) in which the needle 22 is encased and protected in the needle cover 1. FIGS. 7B and 8B show a transition position (Pt) in which the needle 22 is in transition from the first position (P1) to the second position (P2).

(1) In a state where the injection of fluid into a patient, the needle 22 is in the first position in which the needle 22 is exposed before the needle cover 1. This state is shown in FIGS. 7A and 8A.

(2) For moving the needle 22 from the first position to the second position in the same manner as in the above-described, the needle cover 1 is fixed with one hand, and the tube T is withdrawn backward with the other hand to move the tube out of the backward opening 4a of the backward section 4 of the needle cover 1. FIGS. 7B and 8B show a state where the ring-shaped engaging member 27 is passing the backward opening 4a. The engaging member 27 passes the backward section 4 while outwardly expanding the backward section 4 along the slit 7.

In this case, wings 24 and the wing-shaped stoppers 8 move relatively in the opposite directions while being opposed to each other.

(3) In a state where the engaging member 27 moves out of the backward opening 4a (a state where the needle 22 is moved to the second position and is encased in the needle cover 1), the front surface 27a of the engaging member 27 comes into contact with the end surface 4b of the backward section 4 under pressure to be engaged with the end surface 4b as described above.

In the second position, the wing-shaped stoppers 8 are so formed as to slant toward the backward section 4 (slightly upward), thereby when the tube T is withdrawn backward, the wings 24 of the winged needle 21 go over the slanting portion of the stoppers 8 to be engaged with it. In this manner, therefore, the wings 24 and the wing-shaped stoppers 8 come to be engaged with each other, so that the needle 22 is more stably fixed in the needle cover 1.

The outer diameter D1 of the engaging member 27 is greater than the diameter D3 of the backward opening 4a of the backward section 4, and the wings 24 are thus engaged with the stoppers 8, so that the engaging member 27 is kept from moving backward in the direction of the backward section 4 as described above. As explained above, further, the wings 24 are fixed so that they do not move to and fro between the backward section 4 and the stoppers 8. After the needle 22 is encased in the needle cover 1, therefore, there is no possibility that the needle 22 moves back toward the first position to expose its acute needlepoint.

Figure 9A:
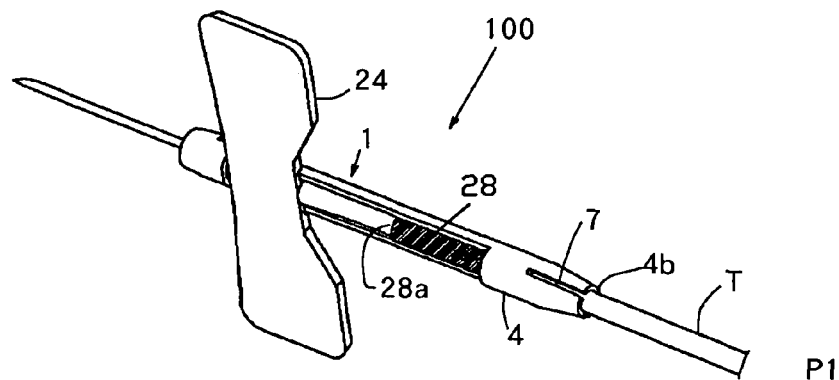
FIGS. 9A to 9C are perspective views showing a use process through time.
Figure 9B:
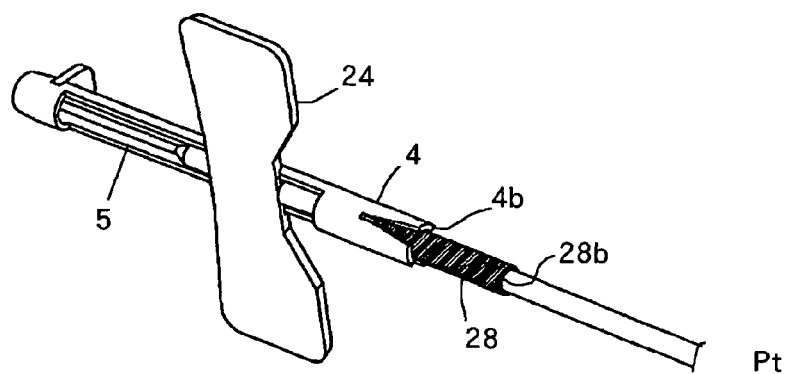
Figure 9C:
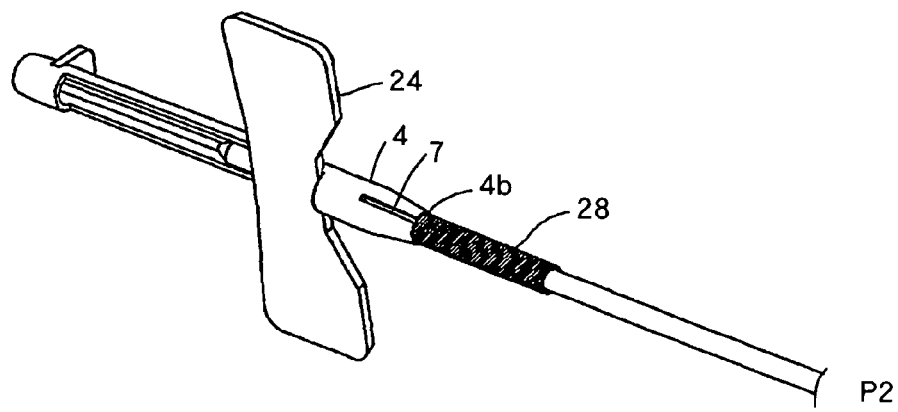

(Method of Use of Guarded Medical Winged Needle Assembly) (iii) (FIGS. 9 and 10)

FIGS. 9 and 10 show an embodiment in which the ring-shaped engaging member 27 in FIGS. 3 to 6 is replaced with a longer pipe-shaped engaging member 28.

In principle, the guarded medical winged needle assembly in this case is handled in the same manner as in the above explanation given with regard to FIGS. 3 to 6. The difference is that the engaging member 28 is formed differently to make the movement more smoothly of the engaging member 28 that passes the backward section 4, compared to the engaging member 27, when the needle 22 moves from the first position (P1) where the needle 22 is exposed from the needle cover 1 to the second position where the needle 22 is encased in the needle cover 1.

That is, the ring-shaped engaging member 27 that is relatively short and nearly cylindrical in FIGS. 3 to 6 is positioned in the middle section 3 (opening 5) when it is in the first position as shown, for example, in FIGS. 3A and 6A. When the engaging member 27 passes through the opening 5 to the backward section 4 to move to the second position, it is liable to be caught on (an opposing end surface of) the backward section 4. For this reason, that portion of the ring-shaped engaging member 27 on the tube side (that is, a portion that may first come in contact with the opposing end surface of the backward section 4) is tapered (or formed in a wedge form) to reduce the degree of being caught, thereby the ring-shaped engaging member can move rather smoothly.

In contrast, in case of the pipe-shaped engaging member 28 that has a relatively large nearly cylindrical form as shown in FIGS. 9 and 10, the backward portion 28b (end surface) of the engaging member is already in the backward section 4 as shown, for example, in FIG. 10A when it is in the first position. When the engaging member 28 moves toward the second position, therefore, it can make a very smooth move, without being caught on (the opposing end surface of) the backward section 4, from its own first position toward the backward opening 4a being inside the backward section 4.

With regard to any other use method, the guarded medical winged needle assembly in this case can be handled substantially in the same manner as in the explanation given with regard to FIGS. 3 to 6, etc., so that a detailed explanation thereof will be omitted.

Figure 11A:
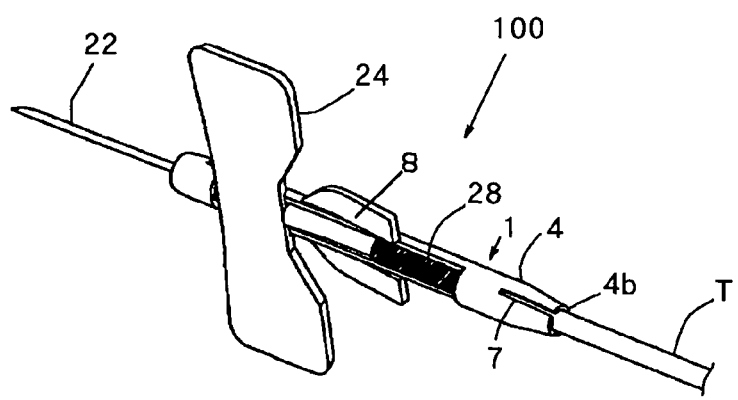
FIG. 11A to 11C are perspective views showing a use process through time.
Figure 11B:
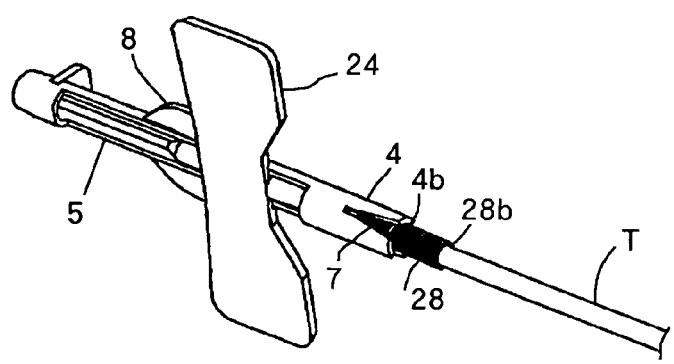
Figure 11C:
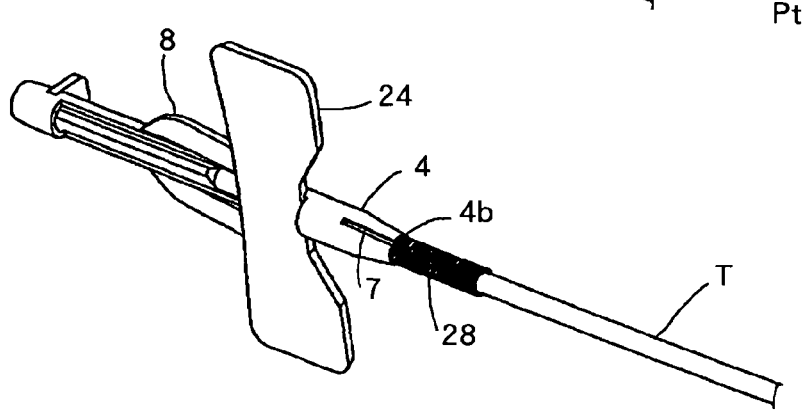

(Method of Use of Guarded Medical Winged Needle Assembly) (iv) (FIGS. 11 to 13)

FIGS. 11 and 12 show an embodiment in which a wing-shaped stoppers 8 is formed on the needle cover 1.

This embodiment corresponds to an embodiment in which the ring-shaped engaging member 27 in FIGS. 7 and 8 (showing the method of use of the embodiment having the wing-shaped stopper 8) is replaced with the pipe-shaped engaging member 28, and the needle assembly in this embodiment can be handled in the same manner as in the above explanation, so that a detailed explanation thereof will be omitted.

Further, FIG. 13 shows an embodiment in which an engaging member 30 is fitted to, or formed on, a backward portion of the hub 23. That is, this embodiment differs from the embodiment shown in FIGS. 3 to 6 only in that the engaging member 30 (equivalent to ring-shaped engaging member 27) is not fitted to, or not formed on, the tube T, but on the backward portion of the hub 23, and the needle assembly can be handled substantially in the same manner as in the explanation with regard to FIGS. 3 to 6, so that a detailed explanation thereof will be omitted.

(Other Embodiments of Guarded Medical Winged Needle Assembly)

The guarded medical winged needle assembly 100 of the present invention includes an embodiment shown in FIGS. 14 and 15. This embodiment similarly comprises a needle cover (or needle guard) 1' having an opening 5 formed in a middle section 3 and a winged needle 21 having a pair of wings 24 fitted to a hub 23, a needle 22 attached to the front portion of the hub 23 and a tube T fitted to a backward portion of the hub 23, and the above winged needle 21 is slidably encased in the above needle cover 1'. In this embodiment, an engaging member 40, 50, 60 having a hook 41, 51, 61, or preferably, a hook 41, 51, 61, is fitted to the above tube T or a backward portion of the above hub 23, thereby the winged needle encased in the needle cover is fixed, as substantially the same manner as described above.

The needle cover 1' is in principle the same as that shown in FIGS. 1A and 1B, and when the tubular member or body is longitudinally divided into a forward section 2, a middle section 3 and a backward section 4, an opening 5 is formed along the middle section 3 in a manner in which a nearly half of the periphery in a cross section of the middle section 3 is removed. Since, however, the engaging member having a hook 41, 51, 61 is used, it is not necessarily required to have a taper in the above backward section 4, nor is it necessary to form a slit at the backward section 4.

(Engaging Member 40, 50, 60)

When the hook 41, 51 is formed in other embodiment of the present invention, there may be employed a constitution as shown in FIGS. 14 and 15, in which a connecting portion 43, 53 is provided to extend from the backward end of a engaging member body 42, 52 and the hook 41, 51 is formed on the backward end of the connecting potion 43, 53. The above connecting portion 43, 53 is fixed to the surface of the hub, thereby through said connecting portion 43, 53, the hook 41, 51 is fixed on the hub. The term "hook" means a portion of any form such as a hook, a barb, a ledge, or the like having an engaging capability.

The number of each of the connecting portion(s) 43, 53 and the hook(s) 41, 51 may be at least one or two, and three to ten of them can be employed. The hook may be a short hook 41 as shown in FIGS. 14A to 14F, or may be a relatively long hook 51 as shown in FIGS. 15A to 15F. Further, there may be employed a constitution in which substantially no connecting portion 43, 53 is provided and the hook 41, 51 is formed directly on the backward portion of the engaging member body 42, 52.

Further, an engaging member 40, 50 (hook 41, 51) may be formed directly on the backward portion of the hub 23 or may be integrally formed on the backward portion of the hub 23 of the winged needle 21.

Like an engaging member 60 exemplified in FIG. 16, further, there may be employed a constitution in which the backward portion (on the tube T side) of a connecting portion 63 is fixed with an annular fixing member 65 and a hook 61 is formed nearly in the center of the above connecting portion 63.

In the above engaging member 40, 50, 60, the connecting portion 43, 53, 63 and the hook 41, 51, 61 sag or deform inwardly or toward an inner diameter of the tube together with the tube when they pass the backward section 4 of the needle cover 1'. And, after passing through it, they return to their original forms, thereby the front surface of the hook 41, 51, 61 (e.g., inwardly extending ledges) is engaged with the backside surface 4b (opening end surface 4b) of the backward section 4 of the needle cover to make a stopper.

Basically, the hook 41, 51, 61 of the engaging member 40, 50, 60 provides an engagement as described above, while the above engaging member 40, 50 has the following tendencies or possibilities. That is, in the engaging member 40, 50, the hub 23 side of the winged needle 21 is fixed with portion 42, 52, while the hook 41, 51 side thereof is not fixed, so that when the winged needle 21 is slidably moved toward the tube T side, the hook 41, 51 may possibly irregularly sag since the connecting portion 43, 53 has a tendency to become a little destabilized. Further, with short hook 41 shown in FIG. 14, it may not slidably move smoothly inside the backward section 4 of the needle cover 1'. These tendencies with the engaging member 40, 50 can be removed or overcome by the engaging member 60 having the annular fixing member 65.

Like the engaging member 27, 28, 30, preferably, the engaging member 40, 50, 60 is formed from a semi-hard thermoplastic resin such as polyethylene, polypropylene, polybutene, polystyrene, a methacrylic resin, polycarbonate, polyvinyl chloride, an ethylene tetrafluoride resin, polyamide, rubber, elastomer, polyethylene terephthalate or the like by, for example, injection molding. The engaging member 40, 50, 60 formed is similarly fitted to the outer surface (circumference) of the hub by a fixing means such as an adhesive.

The engaging member 40, 50, 60 can be formed, integrally with the hub, on the backward or rear end side of the hub when the hub is formed by injection molding, or the like from a semi-hard plastic.

(Engaging Function of Engaging Member 30, 40, 60)

In another embodiment of the guarded medical winged needle assembly of the present invention, when the needle 22 is slidably moved from the first position (Position 1) (e.g., shown in FIG. 14A) where the needle 22 is exposed from the forward section of the needle cover 1' to the second position (Position 2) (e.g., shown in FIG. 14C) where the needle 22 is retracted and hided in the needle cover 1', the hook 41, 51, 61 of the engaging member 40, 50, 60 passes through the inside of the backward section 41 while being inwardly sagged, and after the above needle 22 is moved to the second position, the front surface (or inwardly extending ledges) of the hook 41, 51, 61 is engaged with the backside surface 4b of the backward section 4 (more specifically, is caught on the end surface 4b of the backward opening 4a), thereby the winged needle is fixed in the second position inside the needle cover and is being kept from moving back again toward the first position.

In another embodiment of the guarded medical winged needle assembly of the present invention, when the winged needle 21 is in the first position (e.g., shown in FIG. 14A) where the needle 22 is exposed from the forward section of the needle cover 1', the front surfaces of the above wings 24 is in contact with the backside surface of the forward section 2 in a state where the needle 22 is exposed before the above needle cover, and the above engaging member 40, 50, 60 is positioned in the middle section 3 or the backward section 4. When the winged needle 21 is in the second position (e.g., shown in FIG. 14C) where the needle 22 is encased and hided in the needle cover 1', the needle 22 is positioned in the forward section 2 or the middle section 3, the hook 41, 51, 61 of the engaging member 40, 50, 61 is exposed out of the above backward section 4, and the front surface(s) thereof is engaged with the backside surface 4b of the above backward section 4 (more specifically, caught on the end surface 4b of the opening 4a of the backward section), thereby the winged needle is fixed in the above second position inside the needle cover.

In another embodiment of the guarded medical winged needle assembly of the present invention, preferably, the outer diameter $D_{11}$ of the hook 41, 51, 61 of the engaging member 40, 50, 60, the outer diameter of the tube T, the diameter $D_3$ of the opening 4a of the backward section 4 and the inner diameter $D_4$ of the backward section 4 satisfy the following relationships (i) to (iii), for example, as shown in FIGS. 14 to 16.

Outer diameter $D_{11}$ of hook 41, 51, 61>Outer diameter $D_2$ of tube T    (i)

Outer diameter $D_{11}$ of hook 41, 51, 61>Diameter $D_3$ of opening 4a of backward section 4    (ii)

Outer diameter $D_{11}$ of hook 41, 51, 61>Inner diameter $D_4$ of backward section 4    (iii)

The above backward section 4 of the needle cover 1' may be tapered or may be straight and short in form. Further, the backward section 4 may or may not have a slit. When the above engaging member 40, 50, 60 is employed, the backward section 4 of the needle cover 1' has in principle a short form with no slit, and the front surface(s) of the hook 41, 51, 61 of the engaging member 40, 50, 60 is engaged with the backside surface 4b (end face 4b of the opening 4a) of the backward section 4.

Another embodiment of the guarded medical winged needle assembly of the present invention will be explained below with regard to a use method thereof with reference to drawings.

(Method of Use of Guarded Medical Winged Needle Assembly) (i) (FIG. 14)

Figure 14A:
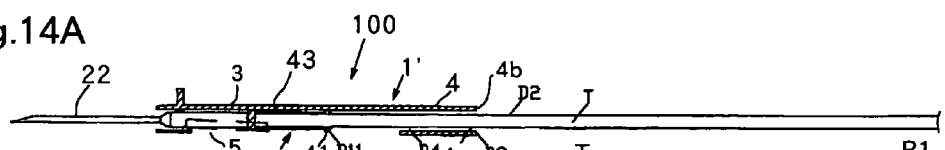
FIGS. 14A to 14C are cross-sectional views showing a use process through time.
Figure 14B:
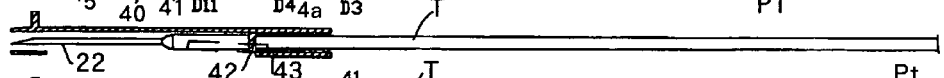
Figure 14C:
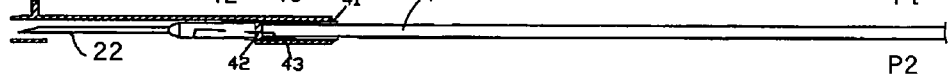
Figure 14D:
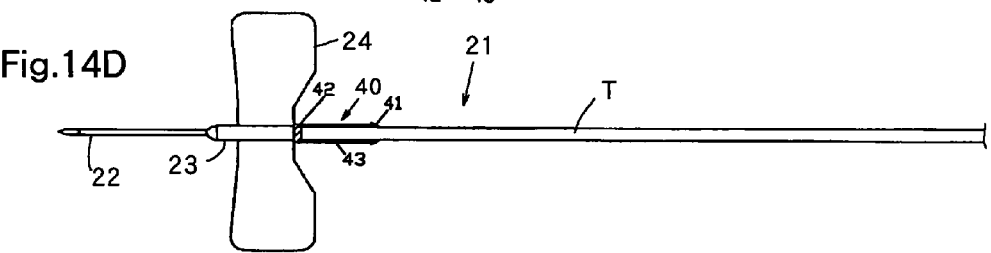
FIG. 14D is a plan view of a winged needle.
Figure 14E:
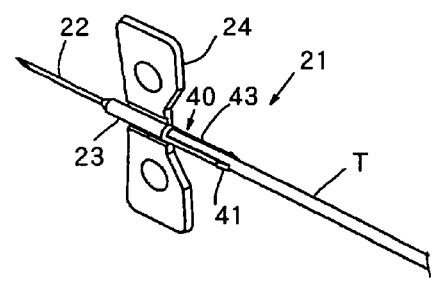
FIG. 14E is a perspective view of the winged needle and FIG. 14F is a perspective view of the same viewed from an opposite side.
Figure 14F:
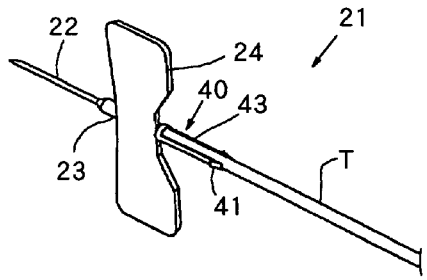
Figure 15A:
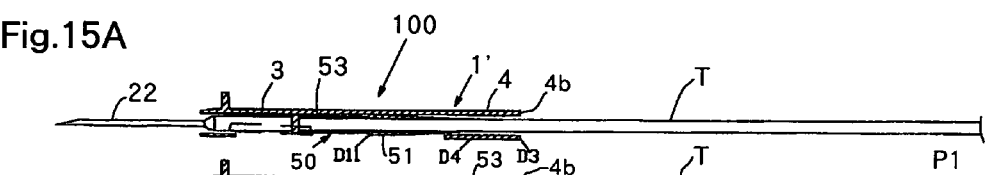
FIGS. 15A to 15C are cross-sectional views showing a use process through time.
Figure 15B:
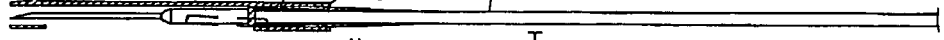
Figure 15C:
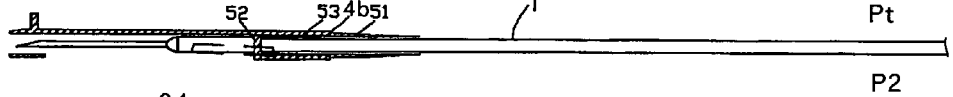
Figure 15D:
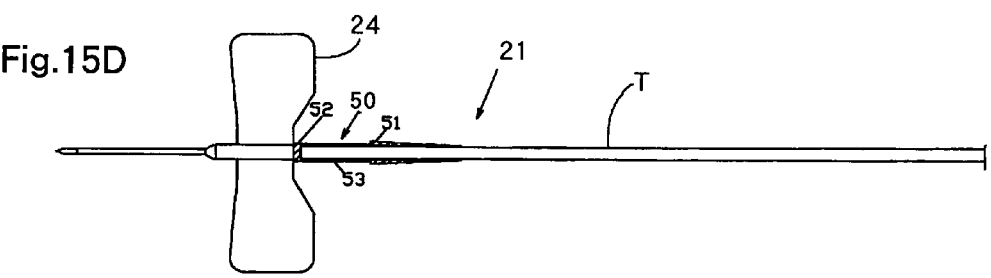
FIG. 15D is a plan view of a winged needle.
Figure 15E:
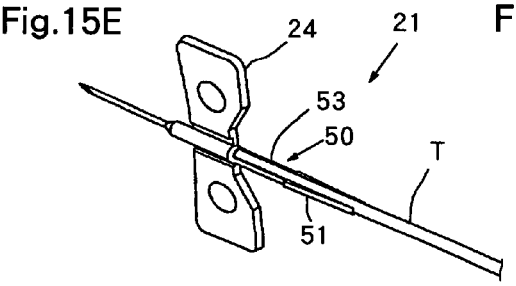
FIG. 15E is a perspective view of the winged needle and FIG. 15F is a perspective view of the same viewed from an opposite side.
Figure 15F:
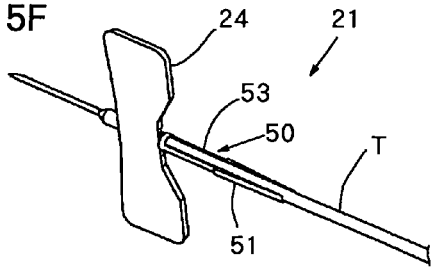

FIG. 14A shows the first position (P1) in which the needle 22 is exposed before the needle cover 1', FIG. 14C shows the second position (P2) in which the needle 22 is encased and protected in the needle cover 1', and FIG. 14B shows a transition position (Pt) in which the needle is in transition from the first position (P1) to the second position (P2).

(1) In a state where the injection of fluid or the like into a patient is completed, the needle 22 is in the first position in which the needle 22 is exposed from the forward section of the needle cover 1'. This state is shown in FIG. 14A.

(2) For moving the needle 22 from the first position to the second position, the needle cover 1' is fixed with one hand, and the tube T is pulled backward with the other hand to withdraw a portion of the tube out of the backward opening 4a of the backward section of the needle cover 1'. The hook 41 of the engaging member 40 moves toward the backward section 4 as shown in FIG. 14B, and it passes through the inside of the backward section 4 while inwardly sagging or deforming. In this case, therefore, the backward section 4 is not required or forced to be expanded outwardly to let the hook 41 to go through, which is a different situation from the case shown in FIGS. 3B and 5B.

(3) After the needle 22 moves to the second position, the front surface (inwardly extending ledges) of the hook 41 is engaged with the backside surface 4*b* of the backward section 4 (end surface 4*b* of the backward opening 4*a*). Since the outer diameter D11 of the hook 41 of the engaging member is larger than the diameter D3 of the opening 4*a* of the backward section 4 as shown by the foregoing relationships, the engaging member 40 stably keeps or prevents the needle 22 from moving back again toward the backward section 4.

After the needle 22 is encased in the needle cover 1', there is no likelihood that the needle 22 moves accidentally from the needle cover 1' to the first position, and exposing its acute needlepoint.

(Method of Use of Guarded Medical Winged Needle Assembly) (ii) (FIG. 15)

FIG. 15 shows an embodiment in which the engaging member 40 in FIG. 14 is replaced with the engaging member 50, and the guarded medical winged needle assembly is handled in the same manner as in the above explanation, and that a detailed explanation thereof will be omitted.

In this embodiment, the hook 51 of the engaging member 50 has a larger length than the hook 41 of the engaging member 40, therefore that the engaging member 50 provide a smoother movement in the backward section 4 and easier engagement than the engaging member 40.

Further, the backward portion (end surface on the tube side) of the engaging member 50 is inside the backward section 4 of the needle cover 1' when the needle is in the first position, thereby the engaging member 50 can smoothly move without being caught on the backward section 4 when the needle moves to the second position.

(Method of Use of Guarded Medical Winged Needle Assembly) (iii) (FIG. 16)

FIG. 16 shows an embodiment in which the engaging members 40 and 50 in FIGS. 14 and 15 are replaced with the engaging member 60.

Figure 16A:
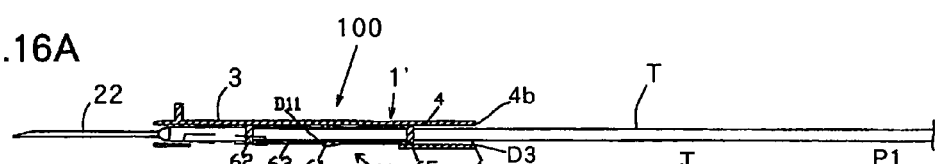
FIGS. 16A to 16C are cross-sectional views showing a use process through time.
Figure 16B:
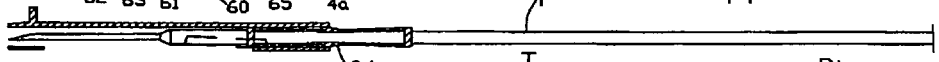
Figure 16C:
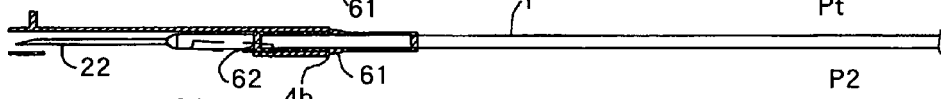
Figure 16D:
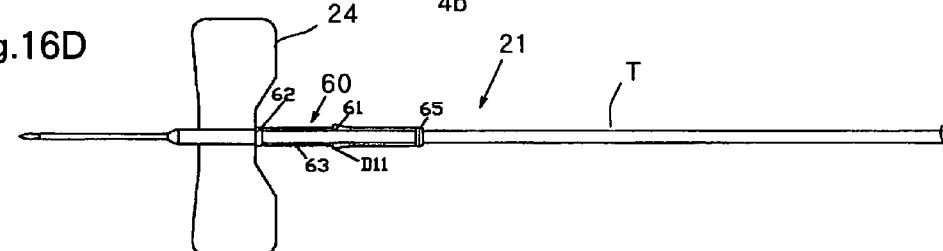
FIG. 16D is a plan view of a winged needle.
Figure 16E:
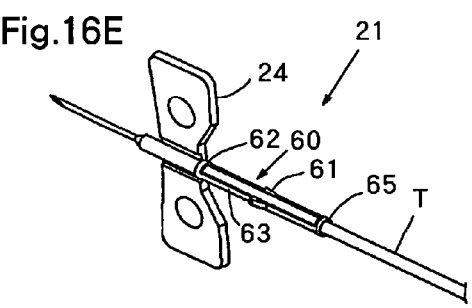
FIG. 16E is a perspective view of the winged needle and FIG. 16F is a perspective view of the same viewed from an opposite side.
Figure 16F:
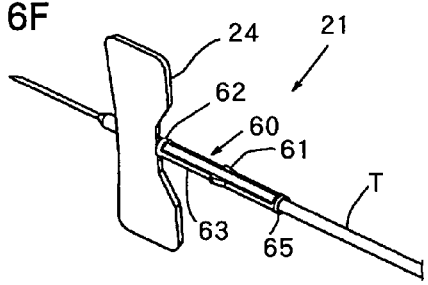

FIG. 16A shows the first position (P1) in which the needle 22 is exposed before the needle cover 1', FIG. 16C shows the second position (P2) in which the needle 22 is encased in the needle cover 1', and FIG. 16B shows the transition position (Pt) in which the needle 22 is in transition from the first position to the second position.

(1) In a state where the injection of fluid or the like into a patient is completed, the needle 22 is in the first position in which the needle 22 is exposed before the needle cover 1' as shown in FIG. 16A.

When the needle cover 1' is fixed with one hand and the tube T is pulled backward with the other hand, the hook 61 of the engaging member 60 moves toward the backward section 4 as shown in FIG. 16B and passes through the inside of the backward section 4 while inwardly sagging.

(3) After the needle 22 moves to the second position (P2), the front surface (inwardly extending ledges) of the hook 61 is engaged with the backside surface (end surface 4*b* of the backward opening 4*a*) of the backward section 4.

Since the outer diameter D11 of the hook 61 of the engaging member is larger than the diameter D3 of the opening 4*a* of the backward section 4 as shown by the foregoing relationships, the engaging member 60 is kept from moving back again toward the backward section 4. After the needle 22 is encased in the needle cover 1', there is no possibility that the needle 22 moves from the needle cover 1' to the first position and exposing its acute needlepoint.

What is claimed is:

1. A guarded medical winged needle assembly comprising:
   a generally cylindrical needle cover having a forward section, a middle section and a backward section in this order in the longitudinal direction of a tubular member, the middle section having an opening formed at the bottom thereof, wherein
   the backward section having a circular backside or edge-face at a far end of the backward section, and
   the backward section being gradually tapered toward the far end of the backward section in its external form or in its internal hollow portion,
   said gradually tapered backward section having at least three slits, each extending from, and cutting, the edge-face at the far end of the backward section which edge-face cutting slits are all capable of opening thereby outwardly expanding the gradually tapered backward section along the opened slits, and
   a winged needle having a pair of wings attached to both sides of a hub, the hub having a substantially uniform outer cylindrical surface, a needle attached to a front portion on said hub and a tube fitted to a backward end portion of said hub,
   said winged needle configured to be housed slidably and protected in said needle cover, said pair of wings slidably projecting out of the opening formed at the bottom of the needle cover, wherein
   said needle slidably moves in the needle cover from a first position wherein said needle is exposed from the forward section of said needle cover to a second position wherein said needle is retracted and hidden in said needle cover, and
   an engaging member having a shape of a straight or tapered ring or pipe (i) is fitted on an outer surface or circumference of said tube at a front end portion thereof, or (ii) is formed or fitted on an outer surface or circumference of the backward end portion of said hub,
   said ring or pipe-shaped engaging member having, on both sides, an annular front end face and backward end face,
   when the needle moves in the needle cover from the first position to the second, said ring or pipe-shaped engaging member passes said backward section with openable, edge-face cutting slits, forcing the slits open, to outwardly expand the backward section along the slits, till said engaging member comes out of the backward section of the needle cover and is exposed, and
   after the needle is moved to said second position, an engagement is established in which the front end face of said ring, or pipe-shaped engaging member is engaged with the circular far end edge-face of said tapered backward section with all slits closed, wherein the entire circular far end edge-face is engaged with the entire front end face of the engaging member, thereby confirming an engagement of the ring or pipe-shaped engaging member with the far end edge-face of said tapered backward section, with the ring or pipe-shaped engaging member exposed and visible out of the needle cover,
   thereby said winged needle is firmly fixed in said second position in said needle cover and kept from moving again toward the first position.

2. The guarded medical winged needle assembly as recited in claim 1, wherein, when said winged needle is in said first position where said needle is exposed from the forward section of said cover, front surfaces of said wings of said winged needle are in contact with a backside surface of said forward section and said engaging member is positioned in said middle section or said backward section, and when said winged needle is in said second position where said winged needle is retracted and hidden in the needle cover, said needle is positioned in said forward section or said middle section, said engaging member is exposed from the far end of said backward section and the front end face thereof is engaged with the far end edge-face of said backward section, thereby said winged needle is being fixed in said second position in said needle cover.

3. The guarded medical winged needle assembly as in either claim 1 or claim 2, wherein said engaging member has an outer diameter (D1), said tube has an outer diameter (D2), the opening of said backward section has a diameter (D3) and said backward section has an inner diameter (D4), and the outer diameter (D1) of the engaging member, the outer diameter (D2) of said tube, the diameter (D3) of the opening of backward section and the inner diameter (D4) of the backward section satisfy the following relationships (i) to (iii), (i) Outer diameter (D1) of the engaging member >Outer diameter (D2) of said tube;

(ii) Outer diameter (D1) of the engaging member >Diameter (D3) of the opening of backward section; and (iii) Outer diameter (D1) of the engaging member ≦inner diameter (D4) of the backward section.

4. The guarded medical winged needle assembly as in either claim 1 or claim 2, wherein the assembly has a pair of stoppers which are protruded on both sides of said middle section for being engaged with the wings.

* * * * *